United States Patent
Sprain et al.

(10) Patent No.: US 12,369,961 B2
(45) Date of Patent: Jul. 29, 2025

(54) CRYOSURGERY SYSTEM

(71) Applicant: Boston Scientific Scimed Inc, Maple Grove, MN (US)

(72) Inventors: Jason W. Sprain, Shoreview, MN (US); Timothy J. Davis, Coon Rapids, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 622 days.

(21) Appl. No.: 16/767,065

(22) PCT Filed: Oct. 17, 2018

(86) PCT No.: PCT/IB2018/058036
§ 371 (c)(1),
(2) Date: May 26, 2020

(87) PCT Pub. No.: WO2019/077508
PCT Pub. Date: Apr. 25, 2019

(65) Prior Publication Data
US 2021/0369319 A1    Dec. 2, 2021

Related U.S. Application Data

(63) Continuation of application No. 15/787,253, filed on Oct. 18, 2017, now abandoned, and a continuation of
(Continued)

(51) Int. Cl.
*A61B 18/02* (2006.01)
*A61B 5/055* (2006.01)
(Continued)

(52) U.S. Cl.
CPC .............. *A61B 18/02* (2013.01); *A61B 5/055* (2013.01); *A61B 34/20* (2016.02);
(Continued)

(58) Field of Classification Search
CPC ............ A61B 18/02; A61B 2018/0023; A61B 2018/00077; A61B 2018/00083;
(Continued)

(56) References Cited

U.S. PATENT DOCUMENTS 5,603,221 A    2/1997   Maytal
6,142,991 A    11/2000   Schatzberger
(Continued)

FOREIGN PATENT DOCUMENTS

CN       1703168 A    11/2005
CN    106456233 A     2/2017

OTHER PUBLICATIONS

Daniels, C. S., & Rubinsky, B. (2011). Cryosurgery with Pulsed Electric Fields. PLoS ONE, 6(11). https://doi.org/10.1371/journal.pone.0026219 (Year: 2011).*
(Continued)

*Primary Examiner* — Joseph A Stoklosa
*Assistant Examiner* — Annie L Shoulders
(74) *Attorney, Agent, or Firm* — Pauly, DeVries Smith & Deffner LLC

(57) ABSTRACT

A cryosurgery system, comprising two or more cryoprobes is provided. Each cryoprobe includes a probe shaft having a distal section insertable in a patient and a proximal coupler. A connector interface with connection ports permits connections to a corresponding cryoprobe. Each connection port can have an isolating sleeve between the proximal coupler and the connection port when the proximal coupler of the respective cryoprobe is inserted in the connection port. The isolating sleeve can include an electrically insulating material so as to electrically isolate each cryoprobe connected to its corresponding connection port from other cryoprobes connected to their corresponding connection ports. An electrical measurement system can be connected to each con-
(Continued)

nection port to detect electrical signals associated with the probe shaft. A control system can detect, based on the electrical signals detected by the electrical measurement system whether the probe shaft is electrically connected to the electrical heater.

19 Claims, 10 Drawing Sheets

Related U.S. Application Data application No. PCT/US2017/057167, filed on Oct. 18, 2017.

(51) Int. Cl.
*A61B 17/00* (2006.01)
*A61B 18/00* (2006.01)
*A61B 34/20* (2016.01)

(52) U.S. Cl.
CPC ............... *A61B 2018/00023* (2013.01); *A61B 2018/00077* (2013.01); *A61B 2018/00083* (2013.01); *A61B 2018/00172* (2013.01); *A61B 2018/0262* (2013.01); *A61B 2018/0293* (2013.01); *A61B 2034/2051* (2016.02)

(58) Field of Classification Search
CPC .. A61B 2018/00172; A61B 2018/0262; A61B 2018/0293; A61B 5/055; A61B 34/20; A61B 2034/2051; A61V 2018/0293
See application file for complete search history.

(56) References Cited

U.S. PATENT DOCUMENTS

| | | | | |
|---|---|---|---|---|
| 7,130,697 | B2 * | 10/2006 | Chornenky | A61N 1/325 606/41 |
| 7,850,682 | B2 * | 12/2010 | Amir | A61B 18/02 606/22 |
| 9,757,196 | B2 * | 9/2017 | Moss | A61B 18/1815 |
| 10,136,942 | B1 * | 11/2018 | Cosman, Jr. | A61B 18/1477 |
| 11,076,906 | B2 * | 8/2021 | Heckel | A61B 18/1206 |
| 2004/0210212 | A1 * | 10/2004 | Maurice | A61B 18/02 606/23 |
| 2004/0215295 | A1 * | 10/2004 | Littrup | F25D 3/10 607/96 |
| 2005/0228367 | A1 * | 10/2005 | Abboud | A61B 18/02 606/20 |
| 2007/0032789 | A1 * | 2/2007 | Gonnering | A61B 18/14 606/49 |
| 2008/0115509 | A1 | 5/2008 | Gullickson et al. | |
| 2012/0089136 | A1 | 4/2012 | Levin et al. | |
| 2012/0265452 | A1 * | 10/2012 | Ramadhyani | A61B 18/02 702/47 |
| 2012/0310230 | A1 * | 12/2012 | Willis | A61N 1/327 606/41 |
| 2016/0367305 | A1 | 12/2016 | Hareland | |

OTHER PUBLICATIONS

International Search Report and Written Opinion received for PCT Patent Application No. PCT/IB2018/058036, mailed on Dec. 10, 2018, 14 pages.

\* cited by examiner

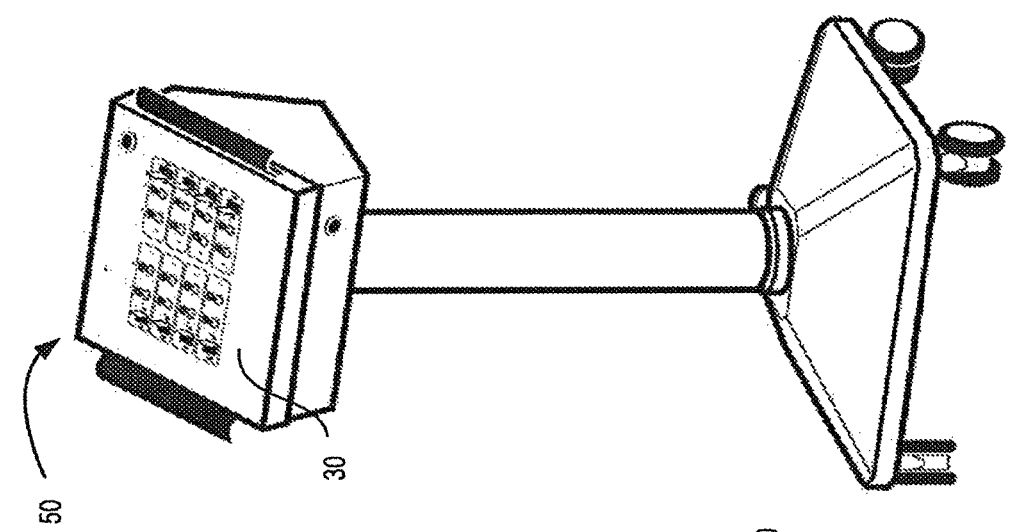
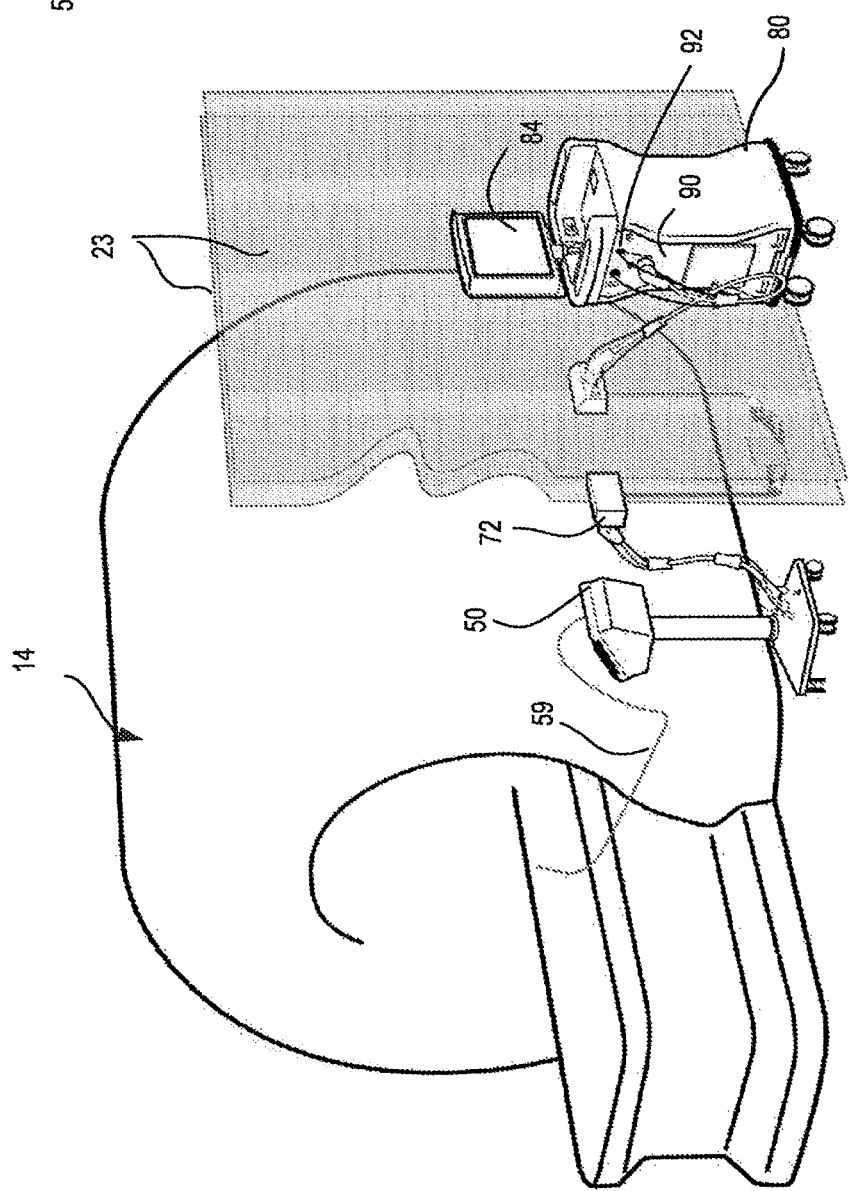
Fig. 2B
Fig. 2A

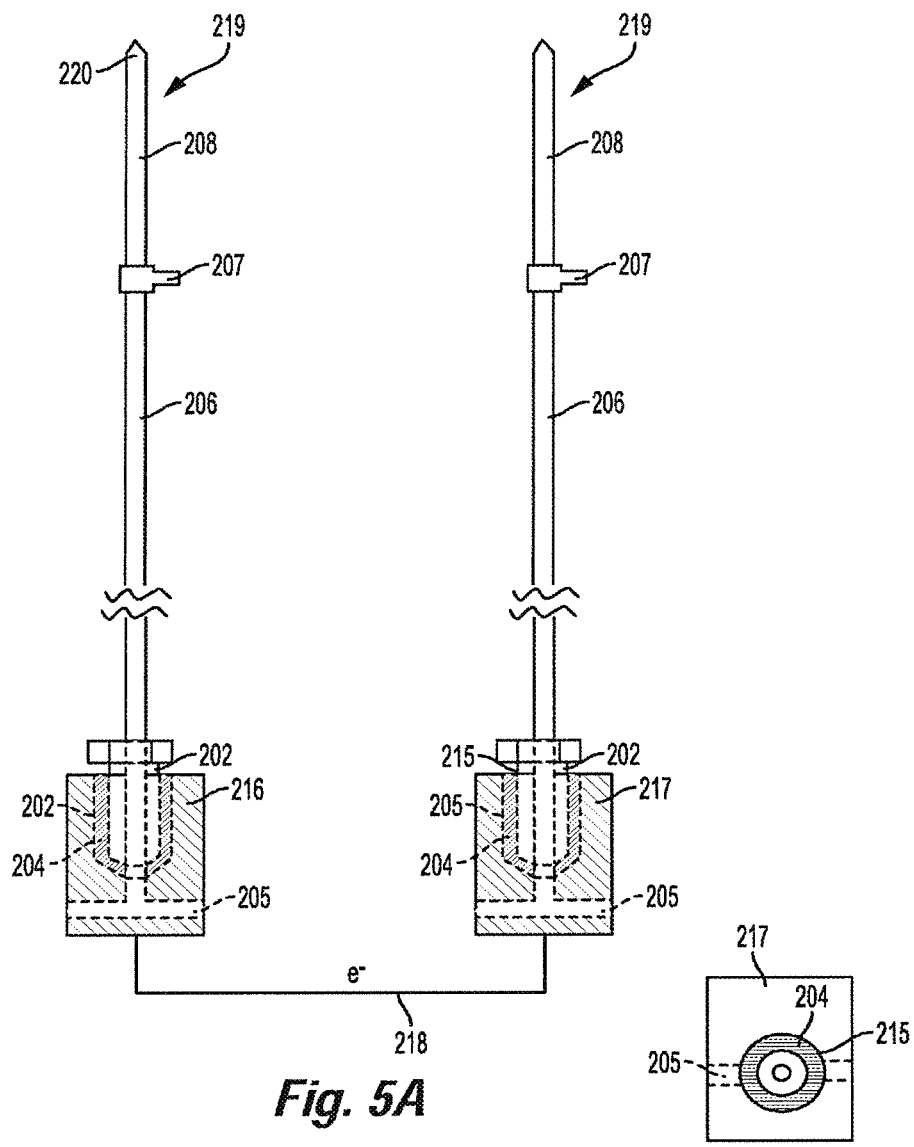

CRYOSURGERY SYSTEM

CROSS-REFERENCE TO RELATED APPLICATION

This application is a U.S. 371 Application of International Application PCT/IB2018/058036, filed Oct. 17, 2018, which claims priority to the International Application PCT/US2017/057167, filed Oct. 18, 2017, and U.S. patent application Ser. No. 15/787,253, filed Oct. 18, 2017, all of which are herein incorporated by reference in their entireties.

BACKGROUND

Cryosurgical systems comprise one or more cryoprobes connected to one or more cryofluid sources. One common use for these systems is the ablation of tissue by subjecting it to freeze thaw cycles. In such systems, the cryofluid is delivered from the cryofluid source to the cryoprobes, where expansion of the cryofluid leads to rapid cooling of the needle tip, thereby freezing tissue in the vicinity of a tip. Such systems are described in the commonly-assigned patent, U.S. Pat. No. 8,066,697 and in published application, U.S. Pub. No. 2010/0256620 A1, the disclosure of which is hereby incorporated by reference in its entirety.

Some cryosurgical systems use Magnetic-Resonance Imaging systems for imaging a patient, for instance to guide the cryoprobes during insertion and/or to obtain images of anatomical features (e.g., tissue, tumor, and the like). An example of such systems can be found in U.S. Pat. No. 7,850,682, the disclosure of which is hereby incorporated by reference. Such systems may be desirable in situations where other imaging systems (such as Computed Tomography) may not be suitable (for instance, if exposure to radiation is not desired). However, placement of the cryosurgical system (having electrically-conductive components) in the vicinity of an MRI system may result in noise and/or electrical interference between the cryosurgical system and the MRI system. Some cryosurgery systems have sought to reduce this problem by separating MRI sensitive components from the rest of the system, for example by operating some control components remote from the MRI magnet.

If multiple cryosurgical tools (e.g., cryoprobes) are connected to the system, the presence of electrically-conductive elements, such as metallic probe shafts, in a time-varying magnetic field (generated by the MRI system) may introduce unwanted currents when they are placed inside a patient. In some instances, the magnitude of these currents may be sufficient to stimulate a nerve, leading to undesirable effects such as spasms or twitching during MRI-guided cryosurgery.

Moreover, some cryosurgical systems may include electrical components such as electrical heaters positioned within the probe shaft of each cryoprobe to thaw tissue after a freezing cycle or to facilitate removal of the cryoprobe from the tissue; or temperature sensors for measuring the temperature of the needle. In such systems, there is a possibility that manufacturing defects or damage due to mishandling may lead to electrical components contacting (e.g., shorting) with the probe shaft. This may lead to electrical signals of undesirable frequencies introduced into the cryosurgery system.

There is a need therefore to provide improved cryosurgical systems, with greater usability in proximity to MRI imaging systems.

SUMMARY

In an aspect, this disclosure is directed to a cryosurgery system, comprising two or more cryoprobes. Each cryoprobe includes a probe shaft having a distal section insertable in a patient. Each probe shaft can comprise an electrically-conductive material and can be configured to receive a cryofluid from a cryofluid source for cooling and/or freezing the patient's tissue. A proximal coupler of the cryoprobe is in electrical communication with a corresponding probe shaft. Two or more connection ports can each permit connections to a corresponding cryoprobe. Connection ports may be connected to housing portions. Each connection port can be fluidly connected to a cryofluid supply line. The system can have one or more electrical insulators which insulate the proximal couplers from each other when they are connected to the connection ports. Each connection port can have an electrical isolator which can be between the proximal coupler and the connection port when the proximal coupler of the respective cryoprobe is inserted in the connection port. The electrical isolator can be a sleeve, which can include an electrically insulating material so as to electrically isolate each cryoprobe connected to its corresponding connection port from other cryoprobes connected to their corresponding connection ports.

In a first embodiment, the present invention provides a cryosurgery system, comprising a first cryoprobe and a second cryoprobe, the first cryoprobe and the second cryoprobe each including a probe shaft, having a distal section insertable in a patient each probe shaft comprising an electrically-conductive material and configured to receive a cryofluid for cooling and/or freezing the patient's tissue, and a proximal coupler at least a portion of the proximal coupler being electrically conductive, the proximal coupler being in electrical communication with the probe shaft; a first connection port configured to receive and connect to the proximal coupler of the first cryoprobe and a second connection port being configured to receive and connect to the proximal coupler of the second cryoprobe, the first connection port and the second connection port each being fluidly connected to a cryofluid supply line for receiving the cryofluid from a cryofluid source and delivering the cryofluid to the proximal coupler of the first cryoprobe and the proximal coupler of the second cryoprobe respectively; the electrically conductive portion of the proximal coupler of the first cryoprobe being insertable into the first connection port, and the electrically conductive portion of the proximal coupler of the second cryoprobe being insertable into the second connection port; and at least one electrical isolator configured to electrically isolate the proximal coupler of the first cryoprobe from the proximal coupler of the second cryoprobe; such that the probe shaft of the first cryoprobe shaft is substantially electrically isolated from the probe shaft of the second cryoprobe.

In some such systems there exists an electrical connection between the first connection port and the second connection port, as described in more detail below.

It is preferred that the system comprises a plurality of such cryoprobes and proximal couplers, as described herein, in this case, the system comprises one or more electrical isolators configured to electrically isolate the proximal couplers of each cryoprobe from that of every other cryoprobe. Particularly, the system comprises at least one electrical isolator per proximal coupler, configured to electrically isolate the proximal coupler of each cryoprobe from the proximal coupler of every other cryoprobe, thereby electrically isolating the probe shaft of each cryoprobe form the probe shaft of every other cryoprobe.

A further embodiment provides a cryosurgery system, comprising a plurality of cryoprobes, each cryoprobe having a probe shaft comprising an electrically-conductive material, the probe shaft being in electrical communication with a proximal coupler; each proximal coupler configured to be received by and couple to a connection port; and one or more electrical isolators configured to electrically isolate each proximal coupler of a cryoprobe from the connection port of every other cryoprobe coupler.

In some cryosurgical systems, the connection ports are or remain, in electrical communication as described below. Thus, in a second embodiment the invention provides a cryosurgery system, comprising a first cryoprobe and a second cryoprobe, the first cryoprobe and the second cryoprobe each including a probe shaft, each probe shaft comprising an electrically-conductive material and configured to receive a cryofluid for cooling and/or freezing the patient's tissue, and a proximal coupler being in electrical communication with the probe shaft; a first connection port configured to receive and connect to the proximal coupler of the first cryoprobe for placing the first cryoprobe in fluid communication with a source of cryofluid, and a second connection port being configured to receive and connect to the proximal coupler of the second cryoprobe, for placing the second cryoprobe in fluid communication with a source of cryofluid, the first connection port being in electrical communication with the second connection port; and an electrical isolator configured to electrically isolate the proximal coupler of the first cryoprobe from the electrical connection between the first and second connection ports.

It is preferred that the system comprises a plurality of such cryoprobes, proximal couplers and connection ports, as described herein, in this case, the system comprises one or more electrical isolators configured to electrically isolate the proximal couplers of each cryoprobe from the electrical connection between its associated connection port and every other connection port. Particularly, the system comprises at least one electrical isolator per proximal coupler, configured to isolate the proximal couplers of each cryoprobe from the electrical connection between its associated connection port and every other connection port, thereby electrically isolating the probe shaft of each cryoprobe from the probe shaft of every other cryoprobe.

In a third embodiment is provided a cryosurgery system, comprising a plurality of cryoprobes arranged in a cryoprobe group each cryoprobe in the cryoprobe group having a probe shaft comprising an electrically-conductive material the probe shaft being in electrical communication with a proximal coupler; each proximal coupler configured to be received by and couple to a connection port; the connection port being in electrical communication with each other connection port of a cryoprobe in the cryoprobe group; and one or more electrical isolators configured to electrically isolate each proximal coupler of a cryoprobe in the cryoprobe group from the connection port of every other cryoprobe coupler of a cryoprobe in the cryoprobe group.

Typically, cryosurgery systems described herein will be cryoablation systems. Such systems typically comprise a plurality of cryoprobes, for example 2, 3, 4, 5, 6, 8 10, 12 or more needles. The needles may be grouped together as a cryoprobe group, which comprises at least two cryoprobes, but may comprise 2, 3, 4, 5, 6, 8 10, 12 or more needles, whose shafts are electrically isolated from each other.

Typically, the cryosurgery systems described herein further comprise a control system that permits supply of the cryofluid to the first cryoprobe and/or the second cryoprobe so as to selectively freeze a tissue. Typically the cryoprobe shafts comprise an electrically conductive material such as a metallic material. A substantial portion of the probe shaft may comprise a metallic material, for example, the whole shaft of the needle can be of a metallic material, e.g., stainless steel. The tips of the needles may also be made of similar material to the shafts.

Typically, fluid connection lines connect the cryoprobes to the proximal couplers and place the proximal coupler in electrical connection with the cryoprobe shaft. The shafts of the cryoprobes are in electrical communication with the proximal coupler because the fluid connection lines are electrically conductive. They are typically required to deliver cryofluid, such as gas, at high pressure and so made of a flexible metallic material, such as a flexible stainless steel. These lines are configured to receive a cryofluid from a cryofluid source and to transfer the cryofluid from the cryofluid source to the cryoprobe for cooling and/or freezing the patient's tissue.

The proximal coupler and the probe shaft are typically both electrically conductive. The proximal coupler is typically in male format, and couples to a female connection port, although a female proximal coupler configured to couple to a male connection port is also possible. The proximal coupler and the probe shaft are each electrically-conductive.

The connection port is configured to receive and couple to the proximal coupler. Each connection port is in fluid communication with a cryofluid supply line, terminating in a connection port cryofluid opening. The connecting port is configured to place the cryoprobe in fluid communication with the cryofluid source, when the proximal coupler is coupled to the port. The connection port is typically adapted to provide a connection that is capable of providing a gas tight connection at high pressures. As used herein, the term "high-pressures" as applied to a gas is used to refer to gas pressures appropriate for Joule-Thomson cooling of cryoprobes and is typically between 3000 psi and 4500 psi.

The connection port is typically in a female connection port configured to receive a male proximal coupler, although a male port adapted to receive a female proximal coupler is also possible.

Female connection ports typically comprise a cavity bounded by an outer wall, having an open end to receive a proximal coupler of a cryoprobe and a connection port cryofluid opening in the outer wall providing a fluid path for a cryofluid to place the cryoprobe in fluid connection with the source of cryofluid.

Male connection ports typically provide a protrusion configured to be received by a female proximal coupler and a connection port cryofluid opening providing a fluid path for a cryofluid to place the cryoprobe in fluid connection with the source of cryofluid.

The connection port cryofluid opening may be closed by a valve whose open condition places the cryoprobe in fluid connection with the source of cryofluid. The valve may be actuated by connection of the proximal coupler to the connection port or may be actuated separately after connection. The connection port may comprise a sealing arrangement co-operating with the proximal coupler to provide a seal that is typically gas tight at high pressure.

There may also be provided a locking mechanism associated with the connection port which holds the union between the connection port and the proximal coupler closed. Such mechanisms can include threaded connectors, over center locking mechanisms or mechanisms in which a spiral groove engages a peg, where rotation of the groove relative to the peg draws the mechanism closed.

In conventional cryosurgery systems, connection ports may be in electrical communication with each other. Typically, this is because each connection port is incorporated into or attached to a housing or housing portion, with which it is in electrical communication. Alternatively, the connection ports may be electrically connected by some other means, such as through mutual connection to another electrically conductive element, such as part of the instrument casing, or through an electrical circuit.

Connecting ports may be arranged in a connecting port group, to connect with a cryoprobe group. A connecting port group is a collection of connecting ports whose corresponding cryoprobes, when connected to the ports, are electrically isolated from each other.

The connection port described herein may be part of a housing, the housing itself typically comprises at least a first housing portion and a second housing portion, each housing portion having a connection port. The housing portions may be connected together to form a unitary housing, or manifold, which comprises a plurality of connection ports. Alternatively, the housing portions may be separated.

Such manifolds form a further embodiment of the invention, which provides a unitary manifold for a cryosurgery system comprising a plurality of connection ports as described herein, each connection port being electrically isolated from the other as described herein.

Where connection ports are electrically connected, this may be as a result of being part of, or connected to, one electrically conductive unitary housing, or manifold, alternatively, the housing portions may be electrically connected by some other means, such as through mutual connection to another electrically conductive element, such as part of the instrument casing, or through an electrical circuit. Typically the manifold comprises at least two connection ports, but may comprise more, for example up to 4, 6, 8 10 12 or more ports.

The manifold may be part of a control system, typically for use remote from an MRI magnet which may additionally comprise components which are not shielded from the effect of operating in proximity with an MRI magnet, or whose functioning may be adversely affected by being close to the MRI, such as microprocessors, computer memory, magnetic storage devices, such as disc drives, etc.

Advantageously, the manifold can be provided as part of a separate connector interface positionable, in use, proximal to the MRI magnet (where MRI sensitive equipment would be adversely affected) within the operating room to permit a plurality of surgical tools such as cryoprobes to be fluidly connected to the cryofluid supply, via an MRI operating room cryofluid supply line. This arrangement isolates parts of the cryosurgery system that may be adversely affected by the MRI magnet and permits them to be placed in a control room remote from the magnet.

The manifold may include a planar surface from which the connection ports can be recessed. The manifold may also include a manifold cryofluid supply line defined as a channel therewithin and in fluid connection with connection port cryofluid openings. In one preferred arrangement, the manifold includes a single common manifold cryofluid supply line common to all connection ports. Alternatively, the manifold may include two or more such supply lines. Each connection port is fluidly connected to the manifold cryofluid supply line such that cryofluid from the cryofluid source is conveyed by the cryoprobe fluid connection lines. The manifold is supplied with cryofluid by one or more cryofluid supply lines.

In a further embodiment, therefore is provided a connector interface for a cryosurgery system for connecting one or more cryofluid supplies, for example in an operating room, to one or more cryoprobes, each cryoprobe having a probe shaft and proximal coupler for coupling the cryoprobe to a connection port, the connector interface comprising: a plurality of connection ports, which may be arranged in a connecting port group, each connection port being connectable to the proximal coupler of a corresponding cryoprobe to place the needle in fluid communication with the cryofluid supply; a plurality of electrical isolator configured to electrically isolate each cryoprobe proximal coupler from every other cryoprobe proximal coupler when coupled the respective connection port of the connecting port group; one or more cryofluid supply lines in fluid communication with the connecting ports; and an operating room cryofluid supply line coupler for connecting an operating room cryofluid supply line and placing the one or more cryofluid supply lines in fluid communication with a cryofluid supply.

In a further embodiment is provided a connector interface for a cryosurgery system for connecting one or more cryoprobes, to a cryofluid supply, each cryoprobe having a probe shaft and proximal coupler for coupling the cryoprobe to a connection port, the connector interface comprising a plurality of connection ports, each connection port being connectable to the proximal coupler of a corresponding cryoprobe to place the needle in fluid communication with the cryofluid supply, one or more of the connection ports comprising an electrical isolator configured to insulate the proximal coupler of a cryoprobe from the connection port; and an electrical circuit configured to detect and/or quantify an electrical potential on the probe shaft or detect an electrical interaction between the probe shaft and an electrical component within the cryoprobe.

The electrical circuit may comprise a sensor configured to be in electrical communication with each corresponding cryoprobe shaft as described herein when a proximal coupler of a cryoprobe is connected to its respective connection port.

In a preferred arrangement, the connection ports and the cryofluid supply lines are arranged as a manifold as described above.

The electrical isolator is generally configured to electrically isolate the proximal coupler of the first cryoprobe from the proximal coupler of the second cryoprobe, such that the first cryoprobe shaft is substantially electrically isolated from the second cryoprobe shaft. The electrical isolator may achieve this in a number of ways. For example, it could be achieved by electrically isolating the connection ports from each other, such as by isolating housing portions comprising a connection port from each other; or by isolating the connection port from the housing portion; or by isolating the proximal couplers from the connection ports. Any combination of these approaches may also be used.

Where connection ports are in electrical connection (for example where the ports are part of a unitary housing or a manifold) the electrical isolator is preferably configured to isolate the proximal coupler from the electrical connection between the ports. This can be achieved, for example, when the connection port comprises an electrical isolator (such as an electrically isolating sleeve), configured to electrically isolate the port from the proximal coupler, or where the proximal coupler comprises an electrical isolator configured to isolate the proximal coupler from the connection port upon connection. When the connection port comprises an electrical isolator, this is preferably in the form of a sleeve, isolating the connection port from the proximal coupler when they are connected. Preferably, the sleeve isolates the outer wall of the connection port from the proximal coupler when they are connected. Preferably, the sleeve covers a substantial portion of an interior surface area of the corresponding connection port.

The isolating sleeve comprises an electrically insulating material such as an electrically non-conductive polymer, such as glass-fiber reinforced polyether ether ketone (PEEK). However, many types of electrically insulating materials can be suitable for use.

Typically all ports comprise an electrical isolator such that all couplers and thereby all probe shafts are isolated from each other.

Electrical isolators (such as an isolating sleeve) as described herein may be discontinuous, for example, they comprise discontinuities such as apertures to permit measurement of electrical signals associated with a proximal coupler connected to the corresponding connection port or to permit a sensor to detect and/or quantify an electrical potential, resistance or current on the proximal coupler or to measure electrical resistance between the shaft of the cryoprobe and an electrical component within the cryoprobe as will be described further below.

Where the connection port comprises a valve, the proximal coupler is optionally electrically isolated from the valve. It is preferred that both the valve as described herein, and the proximal coupler are electrically isolated from the electrical connection between the connection ports by an electrical isolator, preferably by the same electrical isolator, which is preferably in the form of a sleeve isolating the outer wall of the connection port from both the proximal coupler and the valve. The sleeve may therefore be positioned such that when the proximal coupler of the first cryoprobe is connected to the first connection port, the electrical isolator is positioned between the flow control valve connected to the proximal coupler and walls of the first connection port.

To electrically isolate the cryoprobe shafts from each other, it is also possible to provide cryoprobes as described herein, whose proximal coupler comprises an electrical isolator configured to electrically isolate the proximal coupler from the connection port. A further embodiment of the invention therefore provides a cryoprobe having a probe shaft comprising an electrically conductive material and a proximal coupler for coupling the cryoprobe to a connection port for placing the needle in fluid communication with a source of cryofluid, the cryoprobe shaft being in electrical communication with the proximal coupler; the proximal coupler comprising an electrical isolator configured to electrically isolate the proximal coupler of the cryoprobe from the proximal coupler of a second cryoprobe on connection, for example, by isolating the proximal coupler from the connection port.

Electrical components such as heaters and temperature sensors within the cryoprobe shaft, typically receive current from a supply remote from the cryoprobe itself. It is advantageous to be able to detect and quantify the presence of electrical potentials or other electrical signals on the cryoprobe shaft or proximal coupler, and also to detect and quantify the presence of electrical interactions such as unwanted shorts between these electrical components in the cryoprobes, and the probe shafts. The systems described herein therefore may have an electrical circuit configured to detect and/or quantify an electrical potential or other electrical signal on the proximal coupler of the first or second cryoprobe or to detect an electrical interaction between the probe shaft of the cryoprobe and an electrical component within the cryoprobe, as described further below. The electrical circuit can comprise for example, an electrically conductive probe, electrically isolated from the connection port and in electrical connection with the proximal coupler as also described further below.

Thus, in another aspect, the cryosurgery system comprises at least one cryoprobe having an electrical component within the probe shaft. In this aspect, a connector interface having one or more connection ports, each being connectable to the proximal coupler of the corresponding cryoprobe. An electrical measurement system can be connected to each connection port. The electrical measurement system can detect electrical signals associated with the probe shaft. The system also includes a control system configured to detect, based on the electrical signals detected by the electrical measurement system, whether the probe shaft is electrically connected to the electrical heater.

In a further aspect, the connector interface comprises a plurality of electrical resistance measurement systems, each of which is electrically coupled to a corresponding connection port. Each electrical resistance measurement system can be configured to measure electrical resistance between the electrical heater and the probe shaft of the corresponding cryoprobe connected to the corresponding connection port. Each electrical resistance measurement system has electrically-conductive resistance measurement elements that contact at least a portion of the corresponding cryoprobe and thereby be electrically connected with the probe shaft of each corresponding cryoprobe.

Thus, a further aspect provides a cryosurgery system, comprising a cryoprobe having a probe shaft comprising an electrically-conductive material, the probe shaft being in electrical communication with a proximal coupler; the proximal coupler configured to be received by and couple to a connection port for placing the cryoprobe in fluid communication with a cryofluid source; and an electrical sensor configured to detect and/or quantify an electrical potential on the probe shaft or an electrical connection between the shaft and an electrical component within the cryoprobe.

The approach is particularly suitable for use with embodiment and aspects of the invention as described above, such as cryosurgery systems, needles, manifolds and connection interfaces comprising an electrical isolator. Thus, a further embodiment provides cryosurgery systems, cryoprobes manifolds and connection interfaces as described herein, comprising one or more sensors configured to detect and/or quantify an electrical potential or other electrical signal on the probe shaft or to detect and/or quantify an electrical connection between the shaft of the cryoprobe and an electrical component within the cryoprobe.

Conveniently, such sensors are configured to detect and/or quantify an electrical potential or other electrical signal on the proximal coupler(s) of cryoprobe(s) as described herein. A sensor system for this purpose comprises one or more sensors, and may also comprise electrical circuits for the measurement of current, resistance, or voltage and/or one or more control systems configured to determine the presence of a signal indicative of an electric potential on the cryoprobe shaft or a short between the shaft and an electrical component within the cryoprobe. The controller may report either or both of these as an error state and/or shut down the electrical component of the needle or needles, for example.

Such sensors may be configured to be in electrical communication with the cryoprobe shaft. In one approach, the sensor comprises an electrically conductive probe, electrically coupled to a corresponding probe shaft so as to measure electrical signals of the probe shaft. The probes are preferably in electrical connection with the proximal coupler, either directly, such as by touching the coupler, or indirectly, such as by touching the valve which is in electrical contact with the coupler. Probes are preferably electrically isolated from the connection port.

In one embodiment the probe can be an electrically conductive balls or bearings, resiliently biased, held in direct or indirect electrical communication with the coupler by a spring loaded pogo pin.

Typically, the sensor connects to circuitry for measuring an electrical signal on the pin or to detect and or quantify an unwanted circuit between the pin and an electrical component within the needle, to provide a system for detecting unwanted electrical signals on the probe shaft or to detect a short between an electrical component in the needle and the probe shaft.

A further particularly preferred embodiment provides a cryosurgery system, comprising a first cryoprobe and a second cryoprobe, the first cryoprobe and the second cryoprobe each including, a probe shaft, each probe shaft comprising an electrically-conductive material and configured to receive a cryofluid for cooling and/or freezing the patient's tissue, and a proximal coupler being in electrical communication with the probe shaft; a first connection port configured to receive and connect to the proximal coupler of the first cryoprobe and a second connection port being configured to receive and connect to the proximal coupler of the second cryoprobe, and an electrically isolating sleeve within the first and second connection ports, the electrically isolating sleeves configured to electrically isolate the proximal coupler of the first cryoprobe from the proximal coupler of the second cryoprobe; such that the first cryoprobe shaft is substantially electrically isolated from the second cryoprobe shaft.

A further preferred embodiment provides a cryosurgery system, comprising a plurality of cryoprobes each cryoprobe having a probe shaft comprising an electrically-conductive material the probe shaft being in electrical communication with a proximal coupler; each proximal coupler configured to be received by and couple to a connection port; and an electrically isolating sleeve within each connection port configured to electrically isolate each proximal coupler of a cryoprobe from the connection port of every other cryoprobe coupler.

A particularly preferred embodiment provides a cryoablation surgery system, comprising a first cryoprobe and a second cryoprobe, the first cryoprobe and the second cryoprobe each including, a probe shaft, each probe shaft comprising an electrically-conductive material and configured to receive a cryofluid for cooling and/or freezing the patient's tissue, and a proximal coupler being in electrical communication with the probe shaft; a first connection port configured to receive and connect to the proximal coupler of the first cryoprobe for placing the first cryoprobe in fluid communication with a source of cryofluid, and a second connection port being configured to receive and connect to the proximal coupler of the second cryoprobe, for placing the second cryoprobe in fluid communication with a source of cryofluid, the first connection port being in electrical communication with the second connection port; and an electrically isolating sleeve within the connection port configured to electrically isolate the proximal coupler of the first cryoprobe from the electrical connection between the first and second connection ports.

A further particularly preferred embodiment provides a cryosurgery system, comprising a plurality of cryoprobes arranged in a cryoprobe group each cryoprobe in the cryoprobe group having a probe shaft comprising an electrically-conductive material the probe shaft being in electrical communication with a proximal coupler; each proximal coupler configured to be received by and couple to a connection port; the connection port being in electrical communication with each other connection port of a cryoprobe in the cryoprobe group; and an electrically isolating sleeve within each connection port configured to electrically isolate each proximal coupler of a cryoprobe in the cryoprobe group from the connection port of every other cryoprobe coupler of a cryoprobe in the cryoprobe group.

A further particularly preferred embodiment provides a cryosurgery system, comprising a first cryoprobe and a second cryoprobe, the first cryoprobe and the second cryoprobe each including, a probe shaft, each probe shaft comprising an electrically-conductive material and configured to receive a cryofluid for cooling and/or freezing the patient's tissue, and a proximal coupler being in electrical communication with the probe shaft; a first connection port configured to receive and connect to the proximal coupler of the first cryoprobe and a second connection port being configured to receive and connect to the proximal coupler of the second cryoprobe, and an electrically isolating sleeve within each connection port configured to electrically isolate the proximal coupler of the first cryoprobe from the proximal coupler of the second cryoprobe; such that the first cryoprobe shaft is substantially electrically isolated from the second cryoprobe shaft.

The details of one or more examples are set forth in the accompanying drawings and the description below. Other features, objects, and advantages will be apparent from the description and drawings, and from the claims.

BRIEF DESCRIPTION OF DRAWINGS

FIG. 2A is a schematic illustrating connections of a mobile cart and a control system suitable for use with the MRI-guided cryosurgery system of FIG. 1 according to a non-limiting exemplary embodiment;

FIG. 2B is a perspective view of a mobile cart according to a non-limiting exemplary embodiment;

FIGS. 5A, 5B, 5C and 5D each illustrate a simplified view of the manner in which the coupler is electrically isolated from the housing and the manner in which potential on the needle is measured.

FIG. 6A shows a general view of a connector interface and FIG. 6B shows a side view.

DETAILED DESCRIPTION

Cryosurgical systems can be used for cryoablating target tissues (e.g., a tumor). Typically, such systems include one or more cryoprobes, one or more cryofluid sources 60 and a controller. The cryofluid sources 60 can supply gases such as argon, nitrogen, air, krypton, $CO_2$, CF4, xenon, and various other gases. As used herein, "cryofluid" can refer to any fluid that reaches low temperatures (e.g., below 170 Kelvin). In some non-limiting exemplary embodiments, the fluid can reach low temperatures (e.g., below 170 Kelvin) when pressurized to pressures greater than about 1000 psi (e.g., typically around 3500 psi) and permitted to undergo Joule-Thomson expansion, as will be described further below. The cryosurgical system can also include a controller having one or more sensors, flow meters, timers, analog/digital converters, wired or wireless communication modules, etc. Additionally, the controller can also regulate the flow rate, temperature, and pressure of cryofluid supplied to the cryoprobe 100.

During cryosurgery, for instance, a surgeon may deploy one or more cryoprobes to cryoablate a target area of a patient 20 anatomy by placing the cryoprobe 100 at or near the target area of the patient 20 anatomy. In one example, cryoprobe 100 utilizes the Joule-Thomson effect to produce cooling or heating. In such cases, a cryofluid expands in the cryoprobe 100 from a higher pressure to a lower pressure. Expansion of the cryofluid results in temperatures at or below those necessary for cryoablating a tissue in the vicinity of the tip of the cryoprobe 100. Heat transfer between the expanded cryofluid and the outer walls of the cryoprobe 100 can be used to form an iceball, and consequently cryoablate the tissue.

Figure 1:
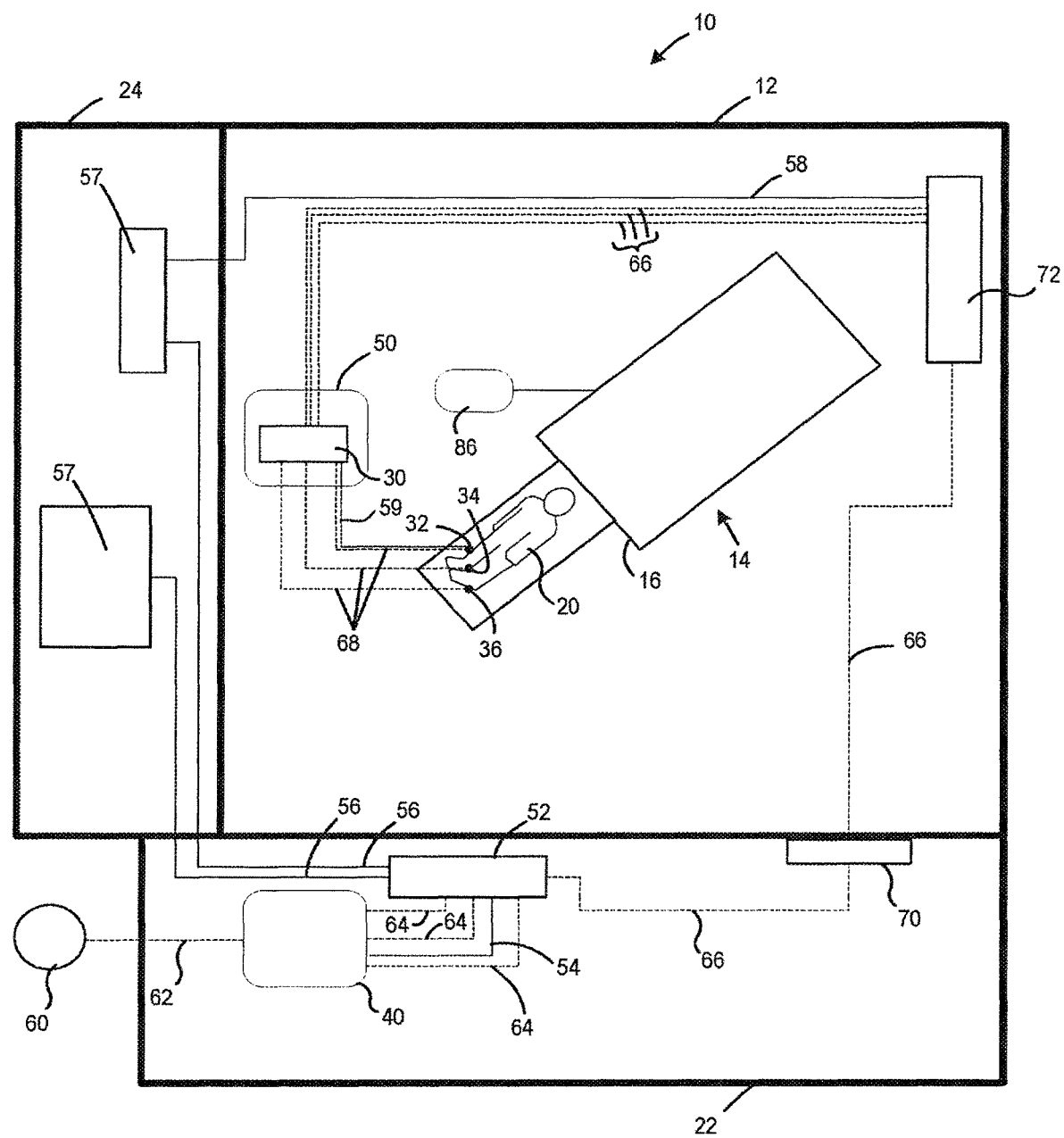
FIG. 1 is a schematic of a Magnetic Resonance Imaging (hereinafter "MRI")-guided cryosurgery system according to a non-limiting exemplary embodiment.

FIG. 1 is a schematic of a Magnetic Resonance Imaging (hereinafter "MRI")-guided cryosurgery system 10 according to a non-limiting exemplary embodiment. The system of FIG. 1 can include a magnet room 12 comprising a MRI scanner 14 comprising a MRI magnet 16 for accommodating a patient 20. The MRI magnet 16 can be of open or closed type, and can include access ports to allow a surgeon to access the patient 20. The MRI magnet 16 can also have electrical connection lines (illustrated by solid lines) and/or mechanical connection lines (illustrated by dashed lines) in FIG. 1 for connecting to various electrical, control and/or cryoablation systems as will be described further below. The system can also include a control room 22 electrically (and/or magnetically) isolated from the magnet room 12 (as shown in FIG. 2A by electrical and/or magnetic isolation 23), and an equipment room 24. The MRI system may be used to image the patient before insertion of surgical tools to visualize patient areas of interest, such as a tumor or a patient cavity. Further, imaging may be performed during insertion to guide the surgical tool to the intended location inside the patient. Additionally, imaging may be performed after insertion and during surgery, as well as after surgery.

Continuing with FIG. 1, in a non-limiting exemplary embodiment, the connection lines may terminate in one or more surgical tools 32, such as cryoprobes insertable inside a patient 20. Accordingly, in some such examples, the system may include a connector interface 30 placed inside the magnet room 12 to permit connection of one or more surgical tools 32, 34, 36 to other components of the cryoablation systems that may be placed outside the magnet room 12 (for instance, in a control room or an equipment room). For instance, the system may include electrical connection lines and fluid connection lines extending from the control room to the magnet room 12, so as to operatively connect a control system 40 to the surgical tools 32. The connector interface 30 can, in some advantageous embodiments, be provided on a cart 50 (which may be stationary or mobile) positioned proximal to the magnet to permit a plurality of surgical tools 32 to be directly or indirectly (e.g., electrically and/or fluidly) connected to the control system 40 positioned outside the magnet room 12 (e.g., in the control room). In the illustrated embodiment, the cart 50 is a mobile cart.

The electrical and fluid connections between the control system 40 and the surgical tools 32 will be described according to an example embodiment. The control system 40 can be electrically connected to a junction box 52 located external to the magnet room 12 by way of a first set of electrical connection lines 54. Further, the junction box 52 can include a second set of electrical connection lines 56 to connect to electrical and/or imaging equipment 57 (such as an imaging router and electrical filters) located external to the magnet room 12 (for instance, within the equipment room). A third set of electrical connection lines 58 may connect the electrical and/or imaging equipment to the connector interface 30 and/or mobile cart 50 located inside the magnet room 12. The junction box 52 can permit removable electrical connection between components in the magnet room 12 and components in the electrical and/or control rooms.

Referring again to FIG. 1, in some examples, the system may be used to perform cryosurgical procedures (e.g., cryoablation). Accordingly in some examples, the system may include one or more cryofluid sources 60. The cryofluid source can be a liquid or gas container that can provide a fluid at cryogenic temperatures and pressures to surgical tools 32 (e.g., cryoprobes). The cryofluid source can be a cooling gas such as argon, nitrogen, air, krypton, $CF_4$ xenon, or $N_2O$.

As can be seen from FIG. 1, the cryofluid source is positioned outside the magnet room 12 and is fluidly connectable to the control system 40 by way of a first set of fluid connection lines 62. The control system 40 in turn can be fluidly connected to the connector interface 30 and/or mobile cart 50 by way of a second set of fluid connection lines 64 and a third set of fluid connection lines 66. A fourth set of fluid connection lines 68 can fluidly connect the surgical tools 32 (e.g., cryoprobes) to the connector interface 30 and/or mobile cart 50. The fluid lines can be flexible and/or detachable and may include other fluid components to regulate pressure of fluid passing therethrough. Fluid from the cryofluid source may thus be conveyed by the set of fluid connection lines 62, 64, 66 and 68 to the surgical tools 32. Optionally, the system can include a fluid connection panel 70 electrically isolated from the magnet room 12 so as to permit fluid connections between components present in the magnet room 12 and those in the control room. Similarly, an electrical connection panel 72 can facilitate electrical connections between components present in the magnet room 12 and those in the control room and/or electrical room.

FIGS. 2A and 2B are schematics of the system 10 and a mobile cart 50 respectively according to a non-limiting exemplary embodiment. Referencing FIG. 2A, connections of the mobile cart 50 and control system 40 are illustrated. The control system 40 can include a mobile housing 80. As shown in FIG. 2A, the housing may include an external display 84. Further, a computer (e.g., processor and memory) may be housed within the housing and operatively coupled to the external display 84. The control system 40 can control the operation of the MRI-guided cryosurgery system 10 according to predetermined operating conditions (e.g., provided as computer-readable programs or instructions) provided by a surgeon (e.g., using input devices such as a keyboard or a touch interface operatively coupled to the control system 40). The external display 84 can be used for displaying data relating to the status of each of the surgical tool and other updated data on the procedure being performed. Further, the external display 84 may provide information relating to the medical record of a specific patient 20. The control system 40 also includes a connection panel 90 to electrically and fluidly connect to the connector interface 30 positioned on the mobile cart 50 located in the magnet room 12. The connection panel 90 can include a plurality of ports 92 that can be fluidly and/or electrically coupled to ports of a connector interface 30 positioned within the magnet room 12. Thus, the control system 40 can individually control operation of each surgical tool connected to a port of the connector interface 30, as will be described further.

Referring back to FIG. 1, the system also includes a MRI display 86 operatively coupled to the MRI scanner 14 and positioned within the magnet room 12 for displaying an image representative of an anatomical feature of a patient 20 so as to provide guidance to a surgeon during surgery. The MRI display 86 can be operatively coupled to electrical and/or imaging components in the equipment room and the control system 40 located within the control room. Such a configuration may display an image identical to the image displayed on the external display 84, and may include information relating to the operating conditions of the overall system. In such cases, advantageously, the MRI display 86 may enable a surgeon to select a desired image, for example, to monitor the progress of the surgical process, images relating to MRI guidance and/or current information relating to one or more surgical tools 32. Optionally, more than one display may be provided in the magnet room 12 to permit simultaneous visualization of various aspects of the surgical procedure.

Figure 3:
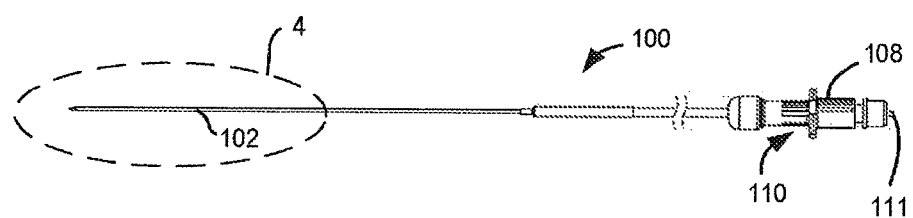
FIG. 3 is a front view of a cryoprobe connectable to the ports of the mobile cart of FIG. 2B according to a non-limiting exemplary embodiment.
Figure 4:
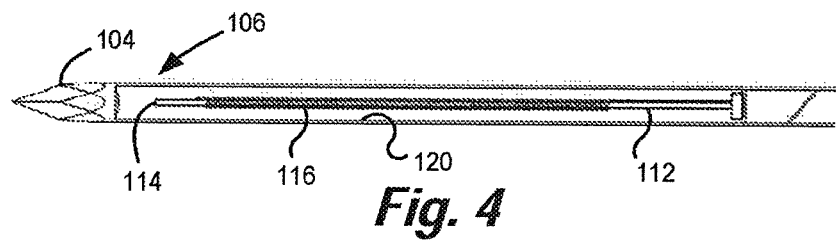
FIG. 4 is a sectional front view of the portion 4 of the cryoprobe of FIG. 3.

As described earlier, the surgical tool can be a cryoprobe 100 in a non-limiting exemplary embodiment. FIG. 3 is a front view of one such cryoprobe 100 and FIG. 4 is a sectional front view of the cryoprobe 100 of FIG. 3. Referring to FIGS. 3 and 4, the cryoprobe 100 can include an elongate body. Components of the cryoprobe 100 can be located within a probe shaft 102. The cryoprobe can, in some cases, be a cryoneedle, in which case, components of the cryoneedle may be arranged interior to a trocar. The probe shaft 102 can terminate in a distal operating tip 104 disposed at a distal section 106 of the cryoprobe 100 for penetrating through tissues of a patient 20 during deployment. In embodiments where the cryoprobe is configured as a cryoneedle, the distal operating tip 104 can penetrate the patient's skin. In alternate embodiments, the cryoprobe can be a flexible probe, and may be inserted by way of a catheter. A proximal coupler 108 can facilitate connections of the cryoprobe 100 to a connector interface 30, control system 40 and/or cryofluid source 60.

The probe shaft 102 can be of substantially thin cross section to allow deployment in tissues of a patient 20. In an example, the cryoprobe can be a cryoneedle, having a probe shaft 102 outer diameter of about 2.1 millimeters. Other dimensions of the probe shaft 102 are also contemplated. For example, the probe shaft 102 can have an outer diameter of between about 1.5 millimeters and about 2.4 millimeters. In addition, in embodiments where the cryoprobe is a cryoneedle, the distal operating tip 104 can be made of a pliant material so as to be flexible (e.g., relative to the proximal portion of the cryoprobe 100) for penetrating soft tissue. Alternatively, a substantial portion of the cryoprobe can be generally flexible and may not pierce the patient skin, and may be flexible (bendable) about its central axis, by a desired angle.

As seen in FIG. 4, the cryoprobe 100 includes a cryofluid supply tube 112 extending substantially along its length for providing a high-pressure cryofluid to the distal operating tip 104. The cryofluid supply tube 112 can be positioned coaxially/concentrically within the probe shaft 102. The cryofluid supply tube 112 can be configured to supply a cryofluid for forming iceballs on an outer surface of the probe shaft 102 over the distal section 106. In some cases, the cryofluid supply tube 112 can be a capillary tube.

With continued reference to FIG. 4, in some examples, the cryoprobe 100 includes a cryocooler. For instance, in the illustrated example, the cryofluid supply tube 112 can terminate in a Joule-Thomson orifice 114. The Joule-Thomson orifice 114 can be positioned near the distal operating tip 104, so as to permit cryofluid exiting the Joule-Thomson orifice 114 to expand into an expansion chamber. Accordingly, a high-pressure cryofluid supplied via the cryofluid supply tube 112 exits through the Joule-Thomson orifice 114 and expands in the expansion chamber. As the cryofluid expands in the expansion chamber, it cools rapidly and forms iceballs of different shapes and/or sizes over the outer surface of the distal operating tip 104. The expansion of the cryofluid can be such that when expanded, the cryofluid is colder than the incoming cryofluid. While an exemplary cryocooler such as a Joule-Thomson orifice 114 is illustrated, it should be understood that other types of cryocoolers such as cryogenic dewars, Stirling-type cooler, pulse-tube refrigerator (PTR), and/or Gifford-McMahon (GM) cooler are contemplated within the scope of the present disclosure. Further, as briefly noted above, cryofluids which may be used for cooling include argon, liquid nitrogen, air, krypton, $CF_4$, xenon, or $N_2O$.

In some advantageous embodiments, the outer surface of the distal operating tip 104 can be made of a heat conducting material such as metal for effectively freezing the patient's tissue. In some such examples, the outer surface of the distal operating tip 104 can be stainless steel or Inconel 620. Other conductive metals and alloys permitting heat exchange between the distal operating tip 104 and the patient tissue are contemplated within the scope of the present disclosure. In addition, a substantial portion of the probe shaft 102 may comprise a metallic material. In some such exemplary embodiments, the probe shaft 102 can comprise an electrically-conductive material. Further, the proximal coupler 108 can also have electrically conductive components (e.g., portions of proximal pin 111) so as to be in electrical communication with a corresponding probe shaft 102.

Referring again to FIG. 4, in some examples, a heater 116 can optionally be provided within the probe shaft 102 to facilitate thawing and/or cauterizing tissue. In some such examples, the heater 116 may be operated after cooling and iceball formation to thaw frozen tissue to facilitate disengagement of cryoprobe 100 therefrom. As illustrated in this exemplary embodiment, an electrical heater 116 can be provided coaxially with the cryofluid supply tube 112 and the probe shaft 102 to facilitate heating the distal section 106 of the cryoprobe 100. Alternatively, the electrical heater 116 can be positioned elsewhere in cryoprobe 100 to heat the distal section 106 of the cryoprobe 100. The electrical heater 116 can be a resistive heater 116, wherein the electrical heater 116 generates heat proportional to the current flow therethrough and the electrical resistance of electrical heater 116. In such cases, as alluded to previously, the control system 40 (shown in FIG. 2A) can supply and/or regulate electrical current flow to the electrical heater 116 within the cryoprobe 100.

In the embodiment illustrated in FIG. 4, the electrical heater 116 comprises metal wire (e.g., titanium, copper and/or alloys such as nichrome) wound in helical coils (e.g., between about 50 coils and about 200 coils) around the cryofluid supply tube 112. For instance, the wire can be wound with a negligible pitch between adjacent coils of the wire. Additionally, the wires can substantially contact an outer surface of the cryofluid supply tube 112. The electric heater 116 may comprise a material having high resistance. For instance, in some advantageous embodiments, the electric heater 116 may have a positive coefficient of electrical resistance such that heat is generated when current passes therethrough. A pair of lead wires may attach to terminal ends of the heater 116 wire, to electrically connect the heater 116 to the control system 40 and supply current thereto. In some such examples, the lead wires, the terminal ends and the heater 116 wire may be bonded or otherwise attached to the cryofluid supply tube 112, and spaced apart from the inner surface 120 of the probe shaft 102 so as to electrically isolate the probe shaft 102 (which may be electrically conductive) from the current carrying heater 116.

Further aspects of the cryoprobe 100 may permit a temperature monitoring and/or control thereof. For instance, the distal operating tip 104 can include at least one thermal sensor for sensing the temperature. Further, the distal operating tip 104 can include proximal handles to facilitate manipulation of the cryoprobe 100, for instance, by a surgeon during cryosurgical procedures. Electrical and/or manual controls on the proximal handle may provide manually controlling distal operating tip 104 and permit functions such as on/off, heating, cooling, and predetermined cycles of heating and cooling by selectively and controllably communicating with the control system 40 and/or cryofluid source. Further, electrical systems may also permit detection of whether a cryoprobe 100 is electrically connected to the control system 40.

As described previously with reference to FIG. 1, the systems described herein and the MRI-guided cryoablation systems described herein and/or certain components of them are positionable proximate to a magnetic resonance imaging (MRI) system that permits imaging to guide insertion of cryoprobes into the patient, during surgery. For instance, the cryoprobes can be connected to the fourth set of electrical connection lines 59 from the mobile cart 50, which in turn can be connected to the connector interface 30. In FIG. 1, one of the surgical tools is shown as being connected to the mobile cart 50 by way of connection line 59, however, substantially all the surgical tools may be connectable to the mobile cart 50 by way of individual connection lines 59.

The cryoprobes, as well as the connector interfaces herein, may include components that are configured to develop reactive effects when exposed to magnetic resonance (MR) signals generated by the MRI system. For example, the metallic material of the probe shaft 102 may develop electric or magnetic fields associated therewith. Alternatively, the electric heater 116 may develop a force as a result of being used in conjunction with (or exposed to) magnetic fields associated with the MRI system (for instance, the magnetic field generated by the MR magnet), and may detach from its attachment (weld or bond) with the cryofluid supply tube 112. This may lead to undesirable physical or electrical contact (e.g., shorting) between the heater 116 and the probe shaft 102.

Further, if two or more cryoprobes are electrically connected, such shorting may generate currents sufficient to stimulate the nerves of a patient 20, and may lead to unintended effects. Accordingly, in some advantageous examples of the present disclosure, the cryoprobes can be electrically isolated from each other. Further, the present disclosure provides an electrical measurement system 420 (similar to sensing arrangement 210) to detect electrical signals, and thereby provide additional information indicative of an electrical contact (e.g., shorting) between the heater 116 and the probe shaft 102.

FIG. 5A is a simplified representation of a connector arrangement according to the invention. In this arrangement, two cryoprobes 219 are connected, individually to connection ports 215 in individual housings 216, 217. The connection ports are in electrical communication with the housings which themselves are in electrical connection 218. As illustrated, the connection ports may refer to receptacles which act as container. The walls of the connection ports thus act as boundaries and define a hollow space to contain portions of the proximal coupler 108, insulating sleeves, and a flow control valve. Alternatively, the connection ports may be a male connector instead of the female receptacle engaging with complementary female connectors on the proximal coupler 108.

Cryoprobe 219 having a probe shaft 208 and a handle arrangement 207 is connected via fluid connection line 205 to a proximal coupler 202 to the connection port 215 within a housing portion 216, 217. The port and housing without the coupler are shown in plan view in FIG. 5D.

Figure 5B:
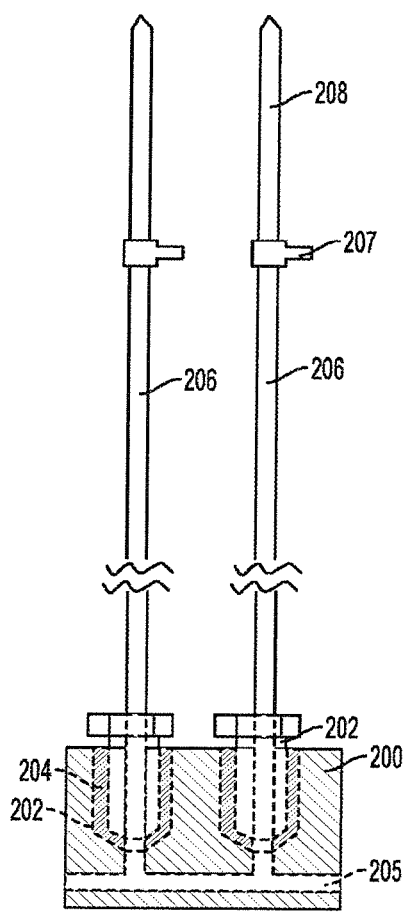

Cryofluid is provided via the manifold 205 to the fluid connection line and thence to the cryoprobe 219. From there, it may be vented to the air or returned to the system via another connection. Both the cryoprobe shaft 208 and the fluid connection line 205 are electrically conductive. The coupler 202, in this case a threaded union, is electrically insulated from the housing portion 216 by an electrically insulating member in the form of a sleeve 204 positioned between the connection port 215, and the union 216 electrically insulates the cryoprobes from each other. FIG. 5B shows a similar arrangement in which the connection ports are arranged in a common housing 200 in which the two housing portions are part of the common housing.

Figure 5C:
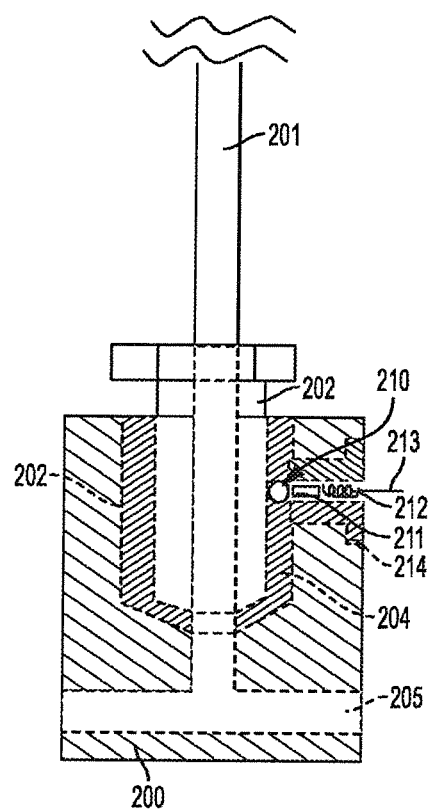

FIG. 5C illustrates a further embodiment of the invention in which the needles are isolated one from another by an insulating sleeve 204, but a sensing arrangement 225, 210, 211, 212, 213 is arranged to measure the electrical potential on the coupler 202 and thus the probe shaft 208. In this case the sensing arrangement is a steel ball 210, held against the coupler 202 by a spring 212, the arrangement held within a threaded cap 214, which insulates the sensing arrangement from the housing, and hence from the other needle(s). The connection 213 is connected to an electrical circuit for measuring the potential on the coupler and hence the needle. The circuit can easily be adapted to measure the resistance between electrical components of the needle and the probe shaft. This can be used to sense unwanted shorts.

Figures 6A, 6B:
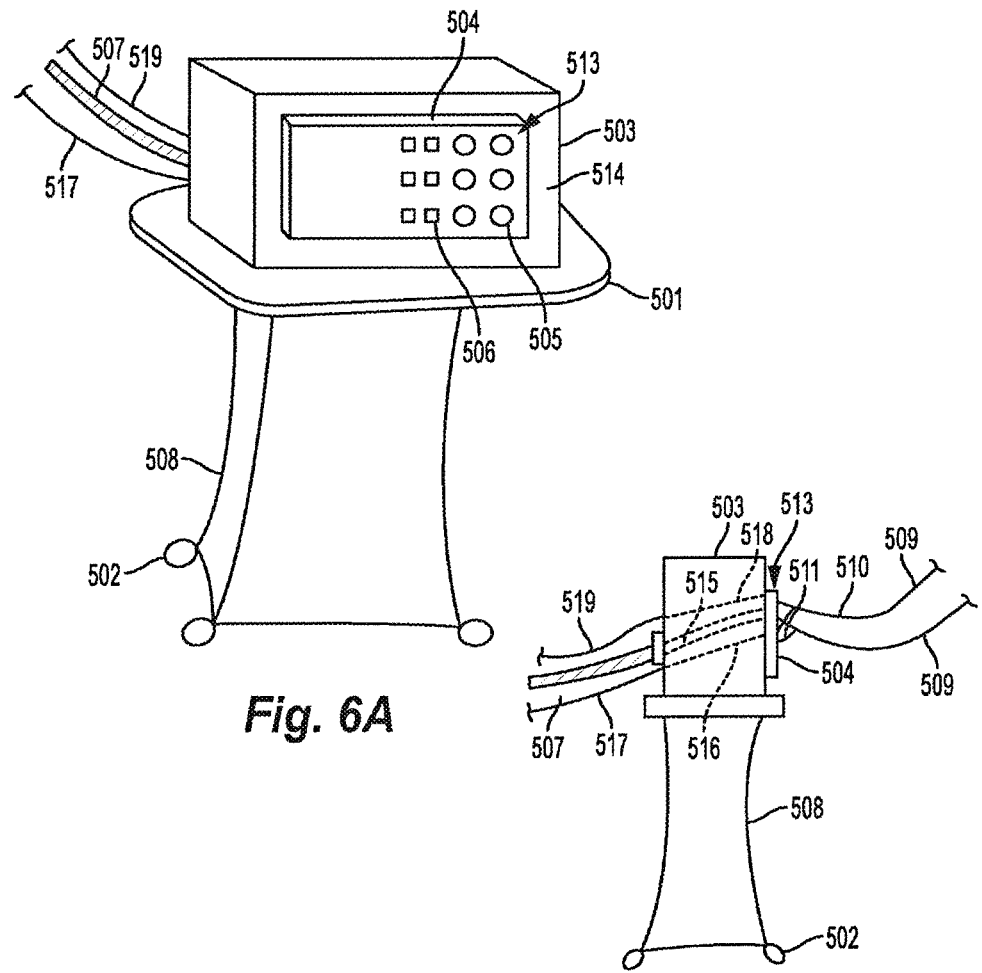
FIGS. 6A and 6B each illustrate is a simplified view of a connector interface mounted on a trolley.

FIG. 6A shows a general view of a connector interface 513, mounted on a trolley 508. Wheels 502, on the bottom of the trolley provide mobility and allow the trolley and the interface to be positioned close to the MRI magnet, whilst other parts of the system remain remote from the MRI. The connector interface rests on a platform 501 on top of the trolley. The connector interface 513 comprises a casing 503, having a manifold 504, on the front face 514. The manifold comprises six connection ports 505, which in this instance are separated from six electrical ports 506. The connection ports 505 connect the proximal connectors of respective cryoprobes to the manifold and allow cryofluid supplied to the connector interface by operating room cryofluid supply line 507 to be delivered to the cryoprobes 509. Electrical ports 506 connect electrical components within the cryoprobes to cryoprobe electrical lines 511.

FIG. 6B shows a side view of the connector interface. This view additionally shows cryoprobes 509, which are connected to the manifold 504. The fluid connection lines 510 connect to the connection ports by proximal couplers (not shown). Bound alongside the fluid supply line, electrical lines 511 connect electrical components of the cryoprobe to the manifold at the electrical port 506. The electrical port is connected via internal electrical line 515, to the operating room electrical lines 517, and thence to the control system. Sensor electrical line 518 connects a sensor (not shown, see FIG. 5C) to electrical sensor lines 516 and electrical sensor operating room lines 519 that connect the sensor to a control system configured to detect whether the probe shaft is electrically connected to the electrical heater and to detect whether an electrical potential is present on the cryoprobe shaft.

Figure 7:
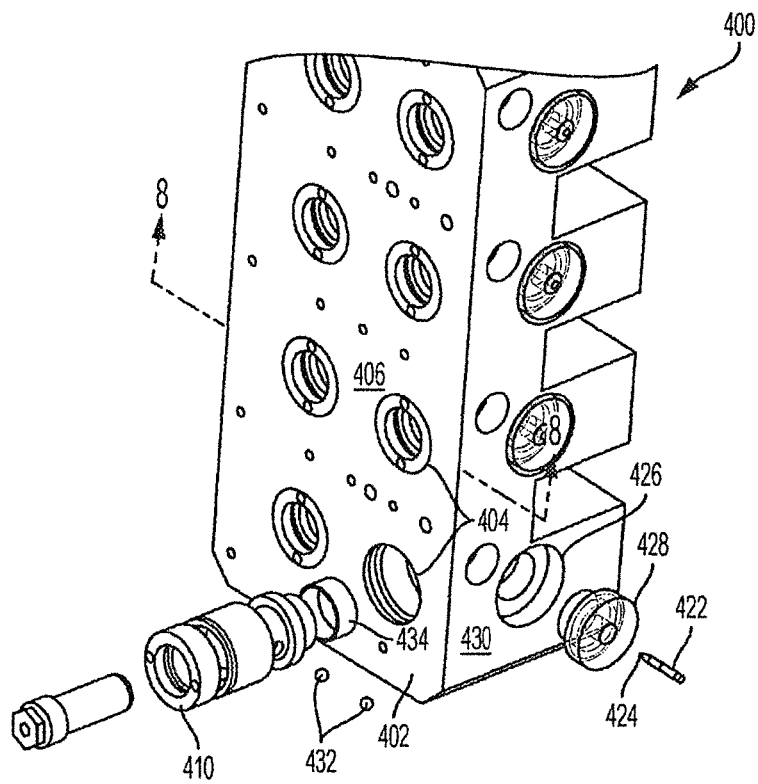
FIG. 7 is an exploded perspective view of a connector interface permitting connection of the cryoprobe of FIG. 3 to the mobile cart of FIG. 2B in accordance with a non-limiting exemplary embodiment.
Figure 8:
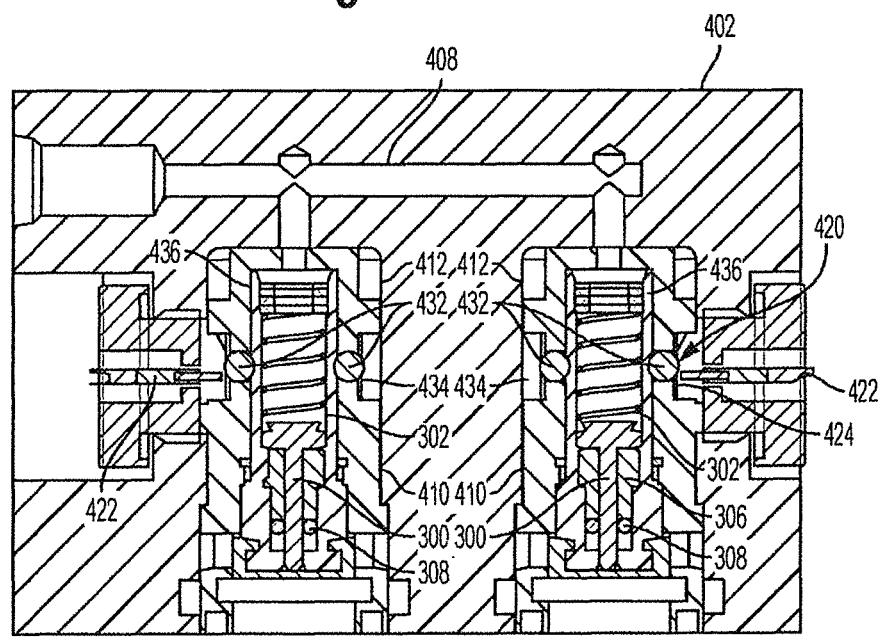
FIG. 8 is a sectional front view of a portion of the connector interface of FIG. 7 taken along the plane 8-8 without cryoprobes connected thereto.

FIG. 7 is an exploded perspective view of a connector interface 400 permitting connection of the cryoprobe 100 of FIG. 3 to the mobile cart 50 of FIG. 2B in accordance with a non-limiting exemplary embodiment, while FIG. 8 is a sectional front view of a portion of the connector interface 400 of FIG. 7. The connector interface 400 can be substantially similar to the connector interface 30 and be provided on the mobile cart 50 positionable within the magnet room 12. The connector interface 400 includes housing portions in the form of a manifold 402 having a connection port 404 for connecting to a cryoprobe 100. The manifold 402 can include a planar surface 406 from which the connection ports can be recessed. As seen in FIG. 8, the manifold 402 includes a cryofluid supply line 409 defined as a channel therewithin. In advantageous embodiments, the manifold 402 may include a single common cryofluid supply line common to all connection ports. Alternatively, the manifold 402 may include two or more cryofluid supply lines. Each connection port 404 can be fluidly connected to the cryofluid supply line 409 such that cryofluid from the cryofluid source 60 (best seen in FIG. 1) is conveyed by the first, second, third and fourth set of fluid connection lines 62, 64, 66, 68 to the cryofluid supply line 409 (seen in FIG. 6). In turn, the cryofluid supply line 409 supplies the cryofluid to the cryofluid supply tube 112 (best seen in FIG. 4) of a cryoprobe 100 connected to the corresponding connection port 404.

With reference to FIGS. 7 and 8, in an aspect of the present disclosure, the connector interface 400 can electrically isolate two or more cryoprobes connectable thereto. Accordingly, as illustrated in FIGS. 7 and 8, each connection port 404 may have an isolating sleeve 410 (similar to sleeve 204) including an electrically insulating material so as to electrically isolate each cryoprobe 100 connected to its corresponding connection port 404 from other cryoprobes connected to their corresponding connection ports. The isolating sleeve 410 is positioned such that when each cryoprobe 100 is connected to a corresponding connection port 404, the isolating sleeve 410 is positioned between the proximal coupler 108 inserted into the connection port 404 and walls 412 of the corresponding connection port 404. In some advantageous embodiments, the isolating sleeve 410 can cover a substantial surface area of the walls 412 of the connection port 404. For instance, the isolating sleeve 410 can occupy between about 90% and about 99.9% of the interior surface area of the walls 412 of the connection port 404. The isolating sleeve 410 can have apertures to permit measurement of electrical signals associated with the probe shaft 102 of a proximal coupler 108 connected to the corresponding connection port 404, as will be described further below.

In some example embodiments, the electrically insulating material of the isolating sleeve 410 is an electrically non-conductive polymer. Advantageously, in some such cases, glass-fiber reinforced polyether ether ketone (PEEK) can be used. However, many types of electrically insulating materials can be suitable for use. While the above configuration provides electrical isolation between two connected cryoprobes, in some advantageous examples, an electrical sensing and/or electrical measurement system 420 may be provided for each connection port 404 so as to detect electrical signals associated with the probe shaft 102 and determine whether the probe shaft 102 is electrically connected to the electrical heater 116. The electrical sensing and/or measurement system 420 (similar to sensing arrangement 210) can be an electrical circuit configured to detect and/or quantify an electrical potential on the proximal coupler, or detect an electrical interaction between the probe shaft of the cryoprobe and the electrical component within the cryoprobe.

FIGS. 7 and 8 illustrate various features of the electrical measurement system 420. The electrical measurement system 420 comprises electrically conductive elements that can contact a portion of a proximal coupler 108 even when isolated by the insulating sleeve. In some exemplary embodiments, only a small portion of the proximal coupler 108 may be available to electrically contact the electrical measurement systems so as to provide substantial electrical isolation between adjacent cryoprobes, while still providing the ability to measure electrical signals associated with the probe shaft 102. For instance, between 0.1% and about 10% of a surface area of the proximal coupler 108 can be in contact with components of the electrical measurement system 420 when the cryoprobe 100 is connected to the connection port 404.

Continuing with FIGS. 7 and 8, the electrical measurement system 420 can, in a non-limiting exemplary embodiment, include a plurality of electrical contact pins 422. Each electrical contact pin 422 can be electrically coupled to a corresponding probe shaft 102 so as to measure electrical signals associated with the probe shaft 102. The electrical contact pin 422 can, in the illustrated embodiment, be a pogo pin terminating in a tip 424 that can indirectly or directly contact the probe shaft 102. Thus, when a proximal coupler 108 of the probe shaft 102 is inserted into the connection port 404, the direct or indirect contact of the tip 424 of the electrical contact pin 422 may electrically connect the electrical contact pin 422 with the probe shaft 102. In the illustrated example, the electrical contact pin 422 has an indirect contact with the probe shaft 102, as will be described further below. Each electrical contact pin 422 can be securely held in a recess 426 in the connector interface 400 by a non-conductive plug 428 at a location suitable to permit the tip 424 of the electrical contact pin 422 to directly or indirectly contact portions of the proximal coupler 108. In the illustrated example, the recess 426 into which the electrical contact pin 422 is inserted is positioned on a surface 430 perpendicular to the planar surface 406 from which the connection ports are recessed.

With continued reference to FIGS. 7 and 8, the electrical measurement system 420 comprises a plurality of electrically-conductive bearings 432 that can be housed at locations corresponding to openings on the isolating sleeve 410. In the illustrated example of FIGS. 7 and 8, the bearings are positioned to contact components housed in or portions of the connection port 404. For instance, in an example, the electrically-conductive bearings 432 contact a flow control valve physically and/or electrically coupled to the proximal coupler 108 (as will be described further below), thereby electrically communicating with the proximal coupler 108 of the corresponding cryoprobe 100. In an embodiment, the probe shaft 102 may be physically coupled to fluid lines that may supply cryofluid to the cryofluid supply tube 112 which may be electrically conductive. As a result, when the probe shaft 102 is exposed to a Mill field, any current induced into the probe shaft 102 may travel to pin 111 of the proximal coupler 108 (and to the corresponding connection port) by way of the electrically conductive fluid lines. A band-shaped spring 434 made of an electrically conductive material may be inserted over the bearings so as to spring-bias the electrically-conductive bearings 432 to contact a corresponding connection port 404. Advantageously, the band-shaped spring 434 can be a constant force spring. In the illustrated example, an inner surface of the band-shaped spring 434 presses against a portion of each bearing at a location opposite (e.g., along the diameter) to the contact between the bearing 432 and the flow control valve 300. An outer surface of the band-shaped spring 434 can permit (e.g., through openings at positions corresponding to) the tip 424 of a corresponding electrical contact pin 422 to contact and/or pass therethrough at locations corresponding to the location of the bearings 432.

The band-shaped spring 434 is electrically conductive and surrounds a substantial perimeter of the isolating sleeve 410, such that the electrical contact pin 422 can contact the band-shaped spring 434 and measure electrical signals at substantially any circumferential position. However, the band-shaped spring 434 extends over a minimal surface area of the isolating sleeve 410 so as to permit the isolating sleeve 410 to electrically isolate connected cryoprobes from each other without substantial electrical interference from the electrical measurement system 420 housed in each connection port 404.

The electrical measurement system 420 can include components that are substantially electrically conductive. For instance, each of the band-shaped spring 434, bearings 432 and electrical contact pin 422 can be electrically conductive. Accordingly, in some examples, the isolating sleeve 410 may have openings to receive the bearings 432 so as to permit electrical measurement. The electrically-conductive bearings 432 are spring-biased by the band-shaped spring 434 to contact a housing 436 (at least portions of which is electrically conductive) of a flow control valve (e.g., a check valve) 300. Accordingly, when a proximal coupler 108 is connected to the flow control valve (as will be described further below), the proximal coupler 108 and the probe shaft 102 (in electrical communication with the proximal coupler 108) are each in electrical communication with the flow control valve 300 and in turn with the electrically conductive housing 436. The flow control valve 300 (best seen in FIGS. 10 and 11) and the electrically conductive housing 436 are each, in turn, in electrical communication with the electrically-conductive bearings 432, electrically connected to the electrical contact pin 422. Thus, the probe shaft 102 is electrically coupled to the corresponding electrical contact pin 422 to permit measurement of electrical signals associated therewith. In some examples, a substantial number of components of the electrical measurement system 420 may be electrically conductive. For instance, the entirety of the electrical contact pin 422, bearings 432 and band-shaped spring 434 may be electrically conductive, and made of a material such as stainless steel, brass or other metals and alloys. Additionally, the manifold 402 may be electrical conductive.

As described previously, components of the cryoprobe 100, such as the proximal coupler 108 and the probe shaft 102 may be electrically conductive, such that the electrical measurement system 420 may be electrically coupled to the probe shaft 102 for measuring electrical signals associated therewith. In further aspects, one or more types of electrical signals (voltage, current, resistance, and the like) can be detected by the electrical measurement system 420. The control system 40 can use such electrical signals to detect whether the electrical heater 116 and the probe shaft 102 are electrically coupler if the signals indicate a "closed" circuit. Alternatively, if the electrical signals are indicative of an "open" circuit, the control system 40 determines that the electrical heater 116 and the probe shaft 102 are electrically isolated.

In an example, the electrical measurement system 420 can measure a voltage associated with the probe shaft 102. As is appreciable, if the electric heater 116 does not short with the probe shaft 102, the electric heater 116 can have a non-zero voltage (because of current supplied thereto during heating), whereas the probe shaft 102 may have a zero voltage. Accordingly, the control system 40 can determine, based on the detected electrical signals (e.g., zero voltage) associated with the probe shaft 102, that it does not electrically communicate with the electric heater 116. Conversely, when the electrical measurement system 420 detects a non-zero voltage of the probe shaft 102, the control system 40 may determine that the electrical heater 116 is in electrical communication with (e.g., shorted) the probe shaft 102.

In alternative embodiments, the electrical measurement system 420 measures resistance associated with the probe shaft 102. For instance, the electrical resistance between the probe shaft 102 and the electrical heater 116 of the corresponding cryoprobe 100 can be measured to determine if the electrical heater 116 has electrical contact (e.g., shorting) with the probe shaft 102. For example, a test voltage can be supplied to the electrical heater 116 and a current passing therethrough can be measured by the electrical measurement system 420, so as to measure electrical resistance associated with the electrical heater 116. In such examples, the change in electrical resistance with time can be monitored by the control system 40 to determine whether the temperature generated by the electrical heater 116 follows predetermined temperature ranges. Predetermined temperature ranges may be known, for instance, based on the material used for the electrical heater 116. The control system 40 may then use such data to determine whether the probe shaft 102 and the electrical heater 116 are electrically isolated. Advantageously, in such embodiments, detection of electrical signals (by the electrical measurement system 420) and determination of whether the electrical heater 116 has electrical communication with the probe shaft 102 (by the control system 40) can be made during operation of the electrical heater 116 (e.g., heating, thawing, etc.) or during operation of MRI system because of electrical isolation between adjacent cryoprobes.

Figure 9:
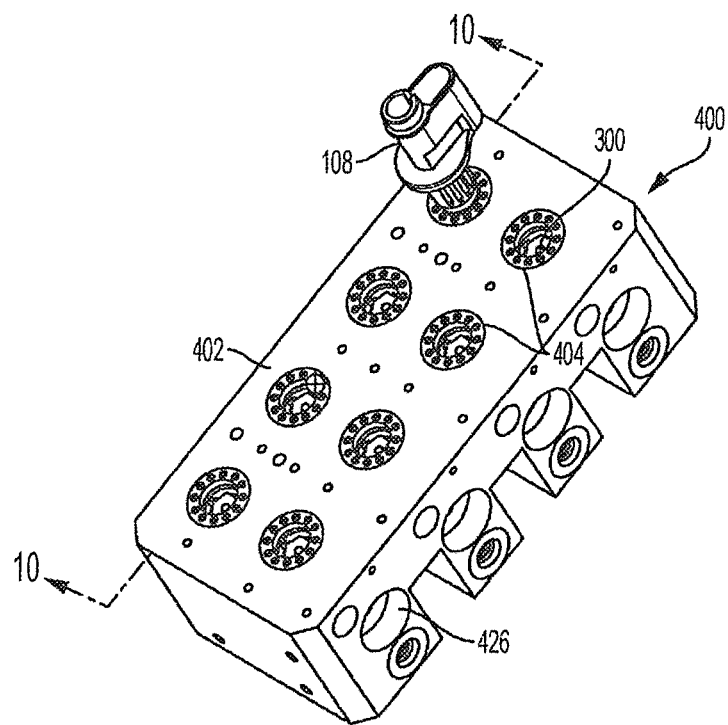
FIG. 9 is a perspective view of the connector interface of FIG. 5 connected to a proximal coupler of a cryoprobe.
Figure 10:
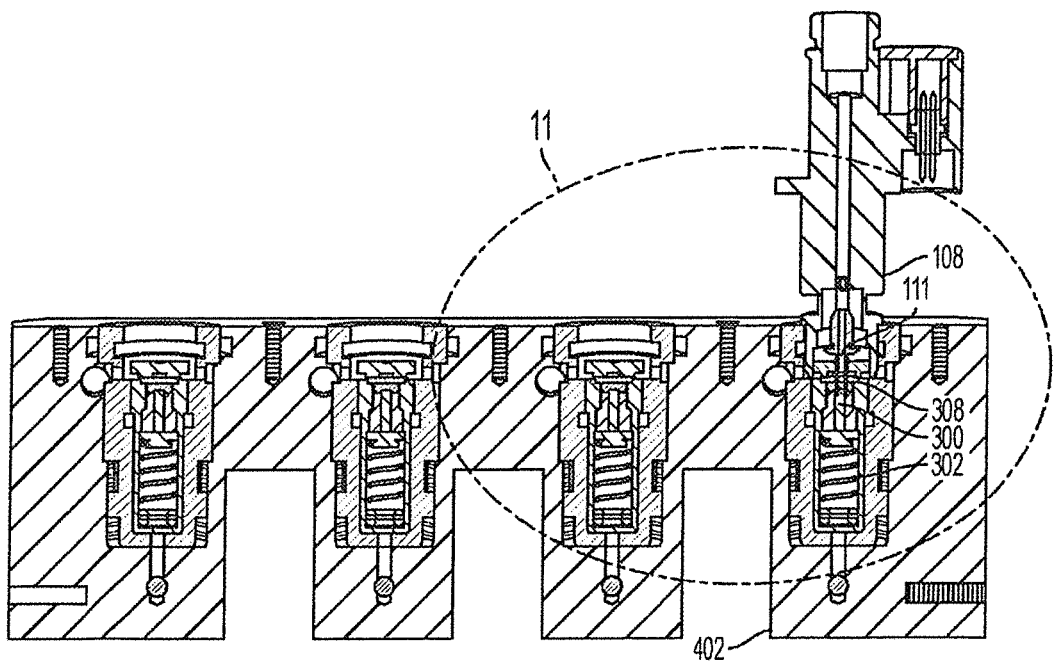
FIG. 10 is a sectional front view of a portion of the connector interface of FIG. 9 taken along the plane 10-10, showing the connector interface connected to a proximal coupler of a cryoprobe.

FIGS. 9-12 illustrate respectively, a perspective view, a sectional front view and an enlarged sectional view of the connector interface 400 of FIG. 7 connected to a proximal coupler 108 of a cryoprobe 100. In FIGS. 9-12, the electrical contact pin and bearings are hidden from view. Referring to FIGS. 9 and 10, when the proximal coupler 108 is connected to the connection port 404, the isolating sleeve 410 is positioned between the proximal coupler 108 and walls 412 of the connection port 404 and substantially surrounds portions of the flow control valve, thereby electrically isolating the proximal coupler 108 (and in turn the probe shaft 102) inserted into the connection port 404. As mentioned before, several components of the connection interface and the cryoprobe 100 can be electrically conductive, whereas the isolating sleeve 410 is electrically insulating. By positioning the isolating sleeve 410 so as to substantially surround the flow control valve, each cryoprobe 100 can thereby be electrically isolated from adjacent cryoprobes and/or electrical components of the connector interface 400, while being in electrical communication with components of the electrical measurement system 420.

Figure 11:
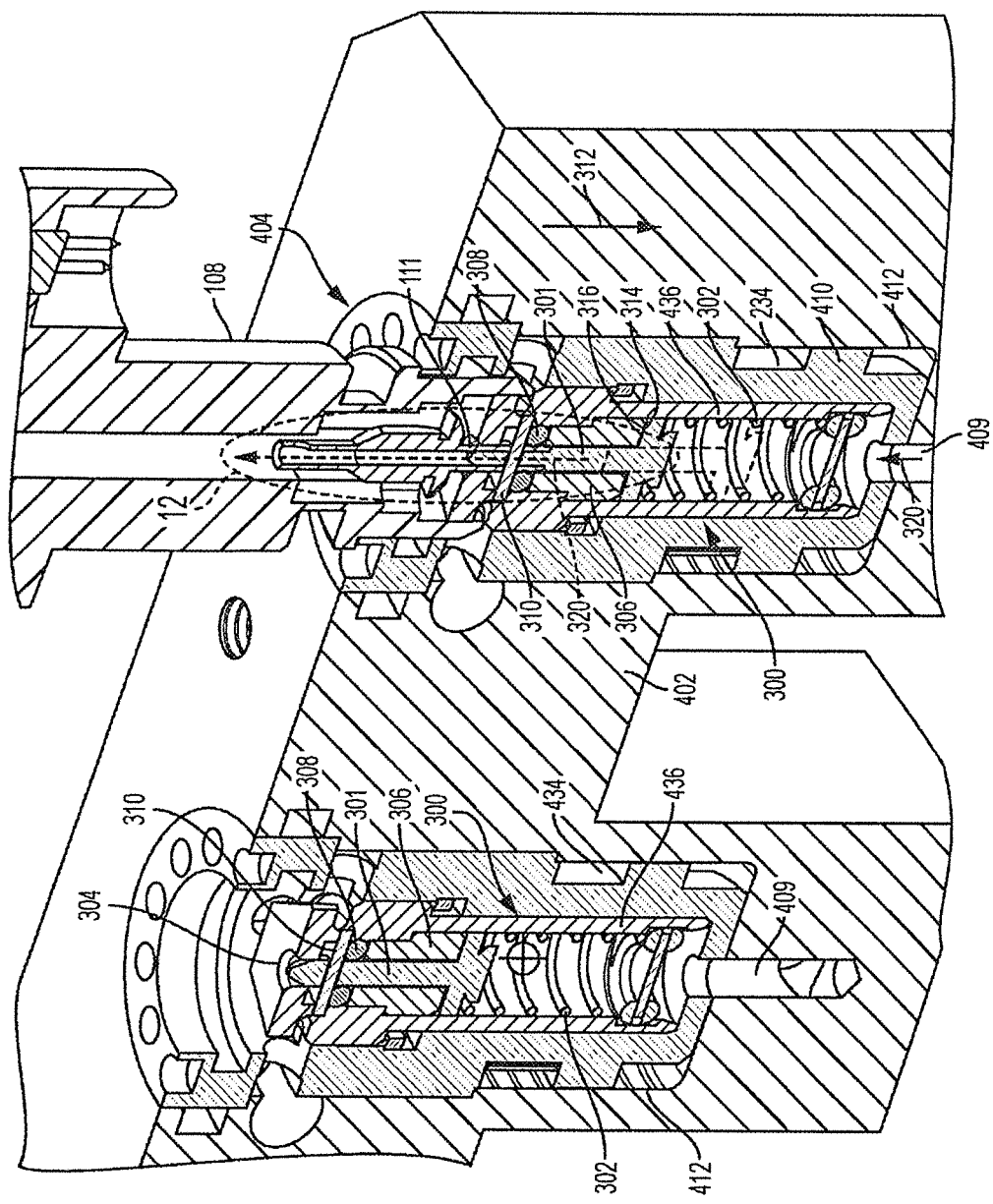
FIG. 11 is an enlarged view of a portion 11 of the connector interface of FIG. 10.
Figure 12:
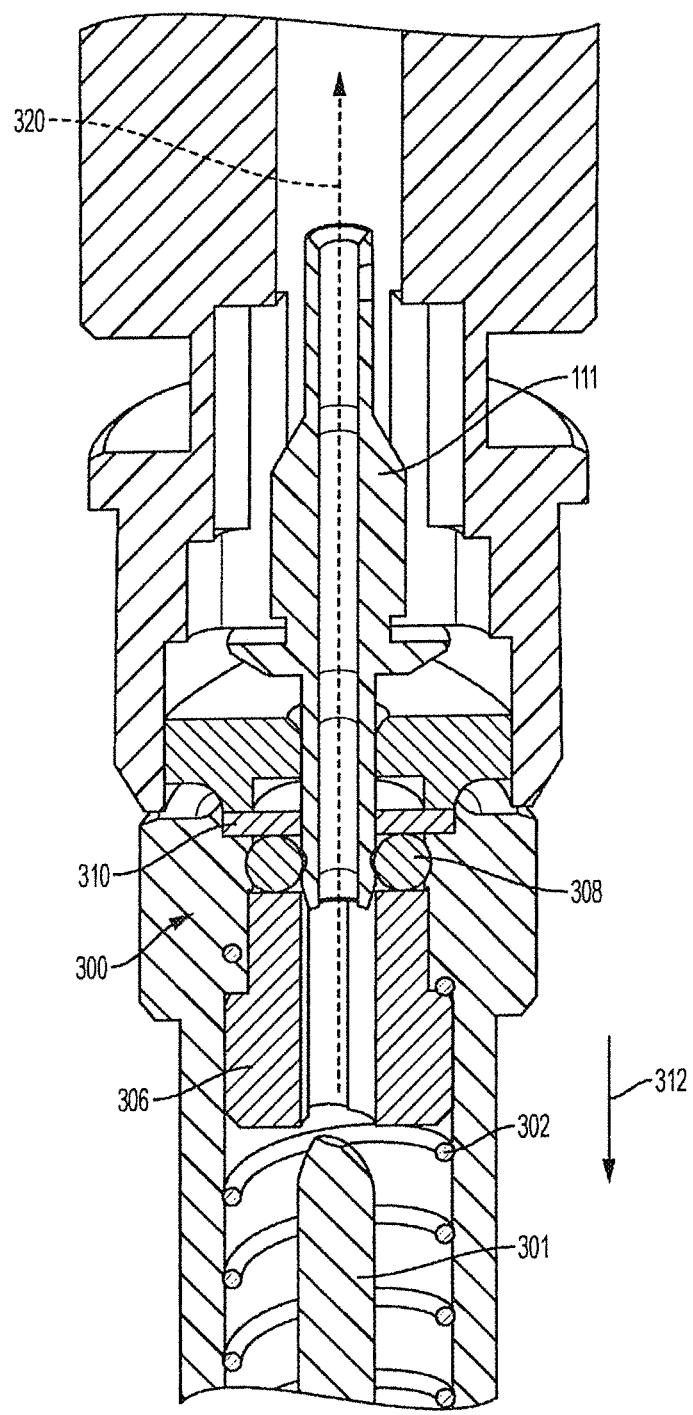
FIG. 12 is an enlarged view of a portion 12 of the connector interface of FIG. 11 illustrating the flow control valve in an open position.

As best illustrated in FIGS. 10 and 11, each connection port 404 comprises a flow control valve 300 connectable to a corresponding proximal coupler 108. The flow control valve can be a spring-loaded check valve comprising a spring-loaded connector pin 301, spring-biased (e.g., by a coil spring 302) to be in a "closed position (shown by solid lines)." In the closed position, the flow control valve may not permit the cryofluid to flow through its outlet 304. A first spacer 306 generally surrounds the spring-loaded connector pin 301. The flow control valve can have a fluid-tight seal by way of seals 308 (e.g., O-rings) positioned between the first spacer 306 and a second spacer 310.

Continuing with FIG. 11, when the proximal coupler 108 of the cryoprobe 100 is inserted into the connection port 404, the proximal pin 111 may be pushed against the spring-loaded connector pin 301, as a result of which, the insertion may exert a force to overcome the spring bias, thereby moving the flow control valve from the "closed position" to the "open position" (shown in FIG. 12) so as to permit flow of cryofluid therethrough. In the illustrated embodiment of FIG. 12, the spring-loaded connector pin 301 may move further away from the proximal pin 111, and into the connection port 404 (shown in FIG. 11) along the direction 312 thereby creating a gap between the planar surface 314 of the spring-loaded connector pin 301, and the planar surface 316 of the first spacer 306. Returning to FIG. 12, the first spacer 306, in turn, may have grooves or apertures to permit fluid flow therethrough (for instance, along direction 320) when the spring-loaded connector pin 301 is moved along the direction 312. When the spring-loaded connector pin 301 moves from the closed position (shown in FIG. 12) to the open position (shown in FIG. 11), cryofluid from the cryofluid supply line 409 can flow toward the proximal coupler 108 and eventually to the cryofluid supply tube of the cryoprobe.

Referring again to FIGS. 11 and 12, when the proximal coupler 108 is inserted into the connection port 404, its proximal pin 111 is received within the aperture of the first spacer 306. The isolating sleeve 410 can, at a minimum, completely electrically insulate an electrically conductive portion of the proximal coupler 108 and the connection port 404 into which that portion of the proximal coupler 108 is inserted. For instance, at least a tip of the proximal pin 111 can be electrically conductive. In such cases, the isolating sleeve 410 completely electrically insulates the tip (or other electrically conductive portions of the proximal pin 111) and the connection port 404.

Embodiments according to the present disclosure provide several advantages. Exemplary embodiments according to the present disclosure permit use of surgical tools with electrically conductive components, such as cryoprobes to be used in conjunction with MRI system. In some advantageous examples of the present disclosure, the cryoprobes can be electrically isolated from each other. Further, advantageously, in such embodiments, detection of electrical signals (by the electrical measurement system) and determination of whether the electrical heater has electrical communication with the probe shaft (by the control system) can be made during operation of the electrical heater (e.g., heating, thawing, etc.) or during operation of MRI system because of electrical isolation between adjacent cryoprobes.

Various examples have been described. These and other examples are within the scope of the following claims.

The invention claimed is:
1. A cryosurgery system, comprising:
a first cryoprobe and a second cryoprobe, the first cryoprobe and the second cryoprobe each including,
a probe shaft having a distal section insertable in a patient, each probe shaft comprising an electrically-conductive material and configured to receive a cryofluid for cooling and/or freezing tissue of the patient, and
a proximal coupler, at least a portion of the proximal coupler being electrically conductive so as to form at least one corresponding electrically conductive portion, the proximal coupler being in electrical communication with the probe shaft, wherein the proximal coupler extends between a proximal end and a distal end, which is closer to the distal section of the probe shaft, wherein the proximal coupler is configured to surround a proximal end of the probe shaft;
a first connection port being configured to receive and connect to the proximal coupler of the first cryoprobe and the proximal end of the first cryoprobe and having an inner surface;
a second connection port being configured to receive and connect to the proximal coupler of the second cryoprobe and the proximal end of the second cryoprobe; and
a first insulator comprising an electrically insulating material, the first insulator is arranged to cover the inner surface of the first connection port to be positioned between the proximal coupler of the first cryoprobe and the first connection port such that the proximal end of the proximal coupler is covered by the first insulator,
the first connection port and the second connection port each being fluidly connected to a cryofluid supply line for receiving the cryofluid from a cryofluid source and delivering the cryofluid to the proximal coupler of the first cryoprobe and the proximal coupler of the second cryoprobe respectively,
the electrically conductive portion of the proximal coupler of the first cryoprobe being insertable into the first connection port, and the electrically conductive portion of the proximal coupler of the second cryoprobe being insertable into the second connection port;
the first insulator being configured to electrically isolate the proximal coupler of the first cryoprobe from the proximal coupler of the second cryoprobe such that the probe shaft of the first cryoprobe is substantially electrically isolated from the probe shaft of the second cryoprobe, the first insulator providing complete electrical insulation between the electrically conductive portion of at least one proximal coupler and a corresponding connection port into which the at least one proximal coupler is inserted, the corresponding connection port being the first connection port or the second connection port.

2. The cryosurgery system of claim 1, having an electrical connection between the first connection port and the second connection port.

3. The cryosurgery system of claim 2, wherein the first insulator is a sleeve positioned within the first connection port and is configured to electrically isolate the proximal coupler of the first cryoprobe from the electrical connection between the first connection port and the second connection port.

4. The cryosurgery system of claim 1, wherein the first insulator comprises an electrically non-conductive polymer.

5. The cryosurgery system of claim 1, further comprising: a second insulator comprising an electrically insulating material, the second insulator is positioned between the proximal coupler of the second cryoprobe and the second connection port such that the proximal end is at least partially covered by the second insulator.

6. The cryosurgery system of claim 1, wherein the distal end of the first proximal coupler is positioned outside the first connection port when the proximal end of the first proximal coupler is positioned within the first connection port.

7. The cryosurgery system of claim 1, wherein the distal end of the first proximal coupler is not covered by the first insulator.

8. The cryosurgery system of claim 1, wherein first insulator occupies 90-99.9% of an interior surface area of walls of the first connection port.

9. The cryosurgery system of claim 1, wherein the first insulator includes apertures to permit measurement of electrical signals associated with the probe shaft connected to the first connection port.

10. A cryosurgery system, comprising:
a cryoprobe comprising:
a probe shaft having a distal section insertable in a patient, the probe shaft comprising an electrically-conductive material and configured to receive a cryofluid for cooling and/or freezing the patient's tissue,
an electrical component housed within the probe shaft, and
a proximal coupler in electrical communication with the probe shaft;
a connection port connectable to the proximal coupler, the proximal coupler is receivable in the connection port with an electrical isolator positioned an interior surface of the connection port and the proximal end of the proximal coupler such that the electrical isolator proximally surrounds the proximal end of the proximal coupler;
wherein the electrical isolator comprises an isolating sleeve configured to insulate the proximal coupler of the cryoprobe from the connection port, the isolating sleeve comprising a plurality of openings; and
an electrical circuit configured to:
detect an electrical potential on the proximal coupler; and determine whether the probe shaft is electrically isolated from the electrical component housed within the probe shaft;

wherein the electrical circuit comprises a plurality of electrically conductive elements electrically coupled to the probe shaft to measure electrical signals of the probe shaft, wherein the plurality of electrically conductive elements are insulated from the connection port and are electrically connected to proximal coupler via the plurality of openings.

11. The cryosurgery system of claim 10, wherein the electrical circuit comprises electrically-conductive bearings that are resiliently biased into electrical contact with the probe shaft.

12. The cryosurgery system of claim 10, wherein the connection port comprises a flow control valve configured to be in electrical connection with the proximal coupler when connected to the connection port.

13. The cryosurgery system of claim 12, wherein each electrically-conductive bearing contacts the flow control valve, thereby electrically communicating with the proximal coupler.

14. The cryosurgery system of claim 10, wherein the electrical circuit is configured to measure voltage of the probe shaft and/or electrical resistance between the probe shaft and the electrical component.

15. The cryosurgery system of claim 10, wherein the electrical circuit is configured to detect electrical signals during operation of the electrical component of the cryoprobe or during operation of a magnetic resonance imaging system configured to image the patient.

16. The cryosurgery system of claim 10, wherein the electrical component housed within the probe shaft comprises a heater and electrical circuit is configured to:
determine that the probe shaft is electrically isolated the heater if the measured electrical signals between the probe shaft and the heater are indicative of an open circuit; and
determine that the probe shaft is not electrically isolated the heater if the measured electrical signals between the probe shaft and the heater are indicative of a closed circuit.

17. A connector interface system for connecting multiple cryoprobes to a cryofluid supply, each cryoprobe having a probe shaft and a proximal coupler for coupling the respective cryoprobe to a corresponding connection port, the proximal coupler extending between a proximal end and a distal end, the connector interface system comprising:
a plurality of connection ports, each connection port being connectable to the proximal coupler of a corresponding cryoprobe to place the cryoprobe in fluid communication with the cryofluid supply,
one or more of the connection ports comprising an electrical isolator comprising a material for electrically insulating the proximal coupler of a cryoprobe from the connection port, wherein the electrical isolator is arranged to cover at least a portion of the proximal end of the proximal coupler, the proximal coupler is receivable in the one or more connection ports with the electrical isolator positioned between an interior surface of the one or more of the connection ports and the proximal end of the proximal coupler such that the electrical isolator radially and proximally surrounds the proximal end of the proximal coupler; and
wherein the electrical isolator comprises an isolating sleeve configured to insulate the proximal coupler of one of the cryoprobes from a respective connection port, the isolating sleeve comprising a plurality of openings; and an electrical circuit configured to:

detect an electrical potential on the probe shaft; and determine whether the probe shaft is electrically isolated from one or more electrical components within the cryoprobe;

wherein the electrical circuit comprises a plurality of electrically conductive elements electrically coupled to the probe shaft to measure electrical signals of the probe shaft, wherein the plurality of electrically conductive elements are insulated from the respective connection port and are electrically connected to proximal coupler via the plurality of openings.

18. The connector interface system of claim 17, wherein the electrical circuit comprises a sensor configured to be in electrical communication with each corresponding cryoprobe shaft when a proximal coupler of a cryoprobe of the one or more cryoprobes is connected to a connection port of the plurality of connection ports.

19. The connector interface system of claim 17, wherein the distal end of the proximal coupler is positioned outside the connection port when the proximal end of the proximal coupler is positioned within the connection port.

* * * * *